US009302245B2

(12) United States Patent
Krull et al.

(10) Patent No.: US 9,302,245 B2
(45) Date of Patent: Apr. 5, 2016

(54) APPARATUS FOR CONTINUOUSLY CARRYING OUT HETEROGENEOUSLY CATALYZED CHEMICAL REACTIONS AT ELEVATED TEMPERATURES

(75) Inventors: Matthias Krull, Harxheim (DE); Roman Morschhaeuser, Mainz (DE); Hans-Juergen Scholz, Alzenau (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 13/497,394

(22) PCT Filed: Sep. 3, 2010

(86) PCT No.: PCT/EP2010/005427
§ 371 (c)(1),
(2), (4) Date: Mar. 21, 2012

(87) PCT Pub. No.: WO2011/035852
PCT Pub. Date: Mar. 31, 2011

(65) Prior Publication Data
US 2012/0178951 A1    Jul. 12, 2012

(30) Foreign Application Priority Data

Sep. 22, 2009   (DE) .......................... 10 2009 042 523

(51) Int. Cl.
| | | |
|---|---|---|
| B01J 19/08 | (2006.01) | |
| B01J 19/12 | (2006.01) | |
| B01J 23/44 | (2006.01) | |
| B01J 23/46 | (2006.01) | |
| B01J 23/882 | (2006.01) | |
| B01J 35/04 | (2006.01) | |
| C07C 29/143 | (2006.01) | |
| C07C 67/03 | (2006.01) | |
| C10G 32/02 | (2006.01) | |
| H05B 6/80 | (2006.01) | |

(52) U.S. Cl.
CPC ............... *B01J 19/126* (2013.01); *B01J 23/44* (2013.01); *B01J 23/462* (2013.01); *B01J 23/882* (2013.01); *B01J 35/04* (2013.01); *C07C 29/143* (2013.01); *C07C 67/03* (2013.01); *C10G 32/02* (2013.01); *H05B 6/806* (2013.01); *B01J 2219/00033* (2013.01); *B01J 2219/0892* (2013.01); *B01J 2219/1215* (2013.01); *B01J 2219/1227* (2013.01); *C07C 2101/14* (2013.01); *C10G 2300/1055* (2013.01); *C10G 2300/202* (2013.01); *C10G 2400/04* (2013.01)

(58) Field of Classification Search
CPC ....................................................... B01J 19/126
USPC .................................................. 422/128, 186
See application file for complete search history.

(56) References Cited

U.S. PATENT DOCUMENTS

| | | |
|---|---|---|
| 1,972,142 A | 9/1934 | Goldstein |
| 2,601,561 A | 6/1952 | Schertz |
| 3,024,260 A | 3/1962 | Ernst |
| 3,050,418 A | 8/1962 | Mendelsohn et al. |
| 3,113,026 A | 12/1963 | Sprung |
| 3,197,473 A | 7/1965 | Klosa |
| 3,395,162 A | 7/1968 | Lamberti |
| 3,585,224 A | 6/1971 | Friedrich et al. |
| 3,652,434 A | 3/1972 | Bar-Nun et al. |
| 3,652,671 A | 3/1972 | Barron |
| 3,682,946 A | 8/1972 | Liechti |
| 3,836,551 A | 9/1974 | Schroeder et al. |
| 4,133,833 A | 1/1979 | Hull |
| 4,165,311 A | 8/1979 | Isowa et al. |
| 4,221,948 A | 9/1980 | Jean |
| 4,339,648 A | 7/1982 | Jean |
| 4,582,933 A | 4/1986 | Mertens et al. |
| 4,675,319 A | 6/1987 | Nardi et al. |
| 4,859,796 A | 8/1989 | Hurtel et al. |
| 4,915,974 A | 4/1990 | D'Amelia et al. |
| 4,994,541 A | 2/1991 | Dell et al. |
| 5,114,684 A | 5/1992 | Walker |
| 5,185,466 A | 2/1993 | Kozulic et al. |
| 5,304,766 A | 4/1994 | Baudet et al. |
| 5,326,538 A | 7/1994 | Walker |
| 5,387,397 A | 2/1995 | Strauss et al. |
| 5,419,815 A | 5/1995 | Doerpinghaus et al. |
| 5,646,318 A | 7/1997 | Dery et al. |
| 5,646,319 A | 7/1997 | Letton et al. |
| 5,710,295 A | 1/1998 | Woodbury et al. |
| 5,830,953 A | 11/1998 | Nishikawa et al. |

(Continued)

FOREIGN PATENT DOCUMENTS

| | | |
|---|---|---|
| CH | 681586 | 4/1993 |
| CN | 1228910 | 9/1999 |

(Continued)

OTHER PUBLICATIONS

International Search Report for PCT/EP2007/008661, Mail dated Jan. 29, 2008.
Translation of International Preliminary Report on Patentability for PCT/EP2007/008681, Jan. 29, 2008.
International Search Report for PCT/EP2007/008680, Mail dated Feb. 15, 2008.
Translation of International Preliminary Report on Patentability for PCT/EP2007/008680, Feb. 15, 2008.
International Search Report for PCT/EP2007/008679, Mail dated Feb. 4, 2008.
International Search Report for PCT/EP2007/008678, Mail dated Mar. 10, 2008.

(Continued)

*Primary Examiner* — Natalia Levkovich
(74) *Attorney, Agent, or Firm* — Tod A. Waldrop (57) ABSTRACT

The invention relates to an apparatus for continuously carrying out heterogeneously catalyzed chemical reactions, comprising a microwave-transparent tube, the longitudinal axis of which extends in the direction of propagation of the microwaves of a single-mode microwave applicator and which is filled with an open-cell foam that carries or is made of catalytically active species.

20 Claims, 1 Drawing Sheet

(56) References Cited

U.S. PATENT DOCUMENTS

| | | |
|---|---|---|
| 5,856,538 A | 1/1999 | Strecker et al. |
| 5,866,531 A | 2/1999 | Assmann et al. |
| 5,892,115 A | 4/1999 | Aizawa et al. |
| 5,988,877 A * | 11/1999 | Hochrad et al. .......... 374/150 |
| 6,017,426 A | 1/2000 | Semeria et al. |
| 6,107,498 A | 8/2000 | Maisonneuve et al. |
| 6,120,741 A | 9/2000 | Jacquault et al. |
| 6,121,471 A | 9/2000 | Scott |
| 6,127,560 A | 10/2000 | Stidham et al. |
| 6,175,037 B1 | 1/2001 | Tweedy |
| 6,291,712 B1 | 9/2001 | Saihata et al. |
| 6,319,187 B1 | 11/2001 | Scott |
| 6,365,885 B1 | 4/2002 | Roy et al. |
| 6,373,040 B2 | 4/2002 | Thomas |
| 6,614,010 B2 | 9/2003 | Fagrell et al. |
| 6,794,510 B2 | 9/2004 | Le Bourdonnec et al. |
| 6,867,400 B2 | 3/2005 | Collins et al. |
| 6,960,627 B2 | 11/2005 | Huth et al. |
| 7,150,836 B2 | 12/2006 | Meikrantz |
| 7,393,920 B2 | 7/2008 | Collins et al. |
| 7,473,739 B2 | 1/2009 | Dairoku et al. |
| 7,759,454 B2 | 7/2010 | Falk et al. |
| 2003/0021793 A1 | 1/2003 | Hilgers |
| 2005/0027120 A1 | 2/2005 | Gojon-Zorrilla |
| 2005/0272631 A1 | 12/2005 | Miracle et al. |
| 2005/0274065 A1 | 12/2005 | Portnoff et al. |
| 2005/0283011 A1 | 12/2005 | Hoong et al. |
| 2006/0057482 A1 | 3/2006 | Yuasa |
| 2006/0228088 A1 | 10/2006 | Charlier de Chily et al. |
| 2006/0252884 A1 | 11/2006 | Falk et al. |
| 2006/0291827 A1 * | 12/2006 | Suib et al. .................. 392/401 |
| 2007/0049721 A1 | 3/2007 | Nefzger et al. |
| 2007/0060762 A1 | 3/2007 | Kawashima et al. |
| 2008/0009541 A1 | 1/2008 | Chambers et al. |
| 2008/0202982 A1 | 8/2008 | Tooley |
| 2008/0264934 A1 | 10/2008 | Moreira et al. |
| 2010/0010244 A1 | 1/2010 | Krull et al. |
| 2010/0032284 A1 | 2/2010 | Krull et al. |
| 2010/0076040 A1 | 3/2010 | Krull et al. |
| 2010/0081843 A1 | 4/2010 | Krull et al. |
| 2010/0116642 A1 | 5/2010 | Krull et al. |
| 2010/0173107 A1 | 7/2010 | Hahn et al. |
| 2011/0083956 A1 | 4/2011 | Krull et al. |
| 2011/0083957 A1 | 4/2011 | Krull et al. |
| 2011/0089019 A1 | 4/2011 | Krull et al. |
| 2011/0089020 A1 | 4/2011 | Krull et al. |
| 2011/0089021 A1 | 4/2011 | Krull et al. |
| 2011/0092722 A1 | 4/2011 | Krull et al. |
| 2011/0137081 A1 | 6/2011 | Krull et al. |
| 2012/0088885 A1 | 4/2012 | Krull et al. |
| 2012/0088918 A1 | 4/2012 | Krull et al. |
| 2012/0090983 A1 | 4/2012 | Krull et al. |
| 2012/0095220 A1 | 4/2012 | Krull et al. |
| 2012/0095238 A1 | 4/2012 | Krull et al. |
| 2012/0103790 A1 | 5/2012 | Krull et al. |
| 2012/0184758 A1 | 7/2012 | Krull et al. |
| 2013/0274368 A1 | 10/2013 | Krull et al. |
| 2013/0289206 A1 | 10/2013 | Krull et al. |
| 2013/0296457 A1 | 11/2013 | Krull et al. |
| 2013/0296458 A1 | 11/2013 | Krull et al. |
| 2014/0200312 A1 | 7/2014 | Krull et al. |

FOREIGN PATENT DOCUMENTS

| | | |
|---|---|---|
| CN | 1351954 | 6/2002 |
| CN | 1749279 | 3/2006 |
| CN | 1931980 | 3/2007 |
| DE | 480866 | 8/1929 |
| DE | 1139738 | 11/1962 |
| DE | 2009156 | 7/1970 |
| DE | 2620638 | 11/1977 |
| DE | 3209800 | 9/1983 |
| DE | 224203 | 7/1985 |
| DE | 102005051637 | 5/2007 |
| DE | 102006047619 | 5/2010 |
| DE | 102009001382 | 9/2010 |
| EP | 0134995 | 3/1985 |
| EP | 0207901 | 1/1987 |
| EP | 0226501 | 6/1987 |
| EP | 0383605 | 8/1990 |
| EP | 0437480 | 7/1991 |
| EP | 0722994 | 7/1996 |
| EP | 0377177 | 7/1997 |
| EP | 0884305 | 12/1998 |
| EP | 1256565 | 11/2002 |
| EP | 1291077 | 3/2003 |
| EP | 1435364 | 7/2004 |
| EP | 1491552 | 12/2004 |
| EP | 1712543 | 10/2006 |
| EP | 1775311 | 4/2007 |
| EP | 2079762 | 6/2007 |
| EP | 1849854 | 10/2007 |
| EP | 1884559 | 2/2008 |
| GB | 0385978 | 3/1931 |
| GB | 0414366 | 7/1934 |
| GB | 0719792 | 12/1954 |
| GB | 2094806 | 9/1982 |
| GB | 2095262 | 9/1982 |
| GB | 2361918 | 11/2001 |
| JP | H02-268660 | 2/1990 |
| JP | 10330338 | 5/1997 |
| JP | 11508873 | 8/1999 |
| JP | 2000-351853 | 12/2000 |
| JP | 2003321427 | 11/2003 |
| JP | 2005322582 | 5/2004 |
| JP | 2006181533 | 12/2004 |
| JP | 2005-002284 | 1/2005 |
| JP | 2005060256 | 3/2005 |
| JP | 2006272055 | 3/2005 |
| JP | 2008031082 | 2/2008 |
| JP | 2009263497 | 11/2009 |
| JP | 2010-207735 | 9/2010 |
| WO | WO 90/03840 | 4/1990 |
| WO | WO 94/18243 | 8/1994 |
| WO | WO 95/06518 | 3/1995 |
| WO | WO 95/09821 | 4/1995 |
| WO | WO 96/14344 | 5/1996 |
| WO | WO 98/29461 | 5/1996 |
| WO | WO 98/29467 | 7/1998 |
| WO | WO 98/39370 | 9/1998 |
| WO | WO 03/014272 | 2/2003 |
| WO | WO 03/016359 | 2/2003 |
| WO | WO 03/041856 | 5/2003 |
| WO | WO 03/090669 | 11/2003 |
| WO | WO 2004/054707 | 7/2004 |
| WO | WO 2004/072031 | 8/2004 |
| WO | WO 2005/033062 | 4/2005 |
| WO | WO 2005/118526 | 12/2005 |
| WO | WO 2006/024167 | 3/2006 |
| WO | WO 2007/065681 | 6/2007 |
| WO | WO 2007/110384 | 10/2007 |
| WO | WO 2007/126166 | 11/2007 |
| WO | WO 2008/043492 | 4/2008 |
| WO | WO 2008/043493 | 4/2008 |
| WO | WO 2008/043494 | 4/2008 |
| WO | WO 2008/043495 | 4/2008 |
| WO | WO 2009/002880 | 12/2008 |
| WO | WO 2009/064501 | 5/2009 |
| WO | WO 2009/121490 | 10/2009 |

OTHER PUBLICATIONS

Translation of International Preliminary Report on Patentability for PCT/EP2007/008678, Mar. 10, 2008.
International Search Report for PCT/EP2007/008677, Mail dated Mar. 3, 2008.
Translation of International Preliminary Report on Patentability for PCT/EP2007/008677, Mar. 3, 2008.
International Search Report for PCT/EP2009/001989, mail dated Jun. 10, 2009.
Translation of International Preliminary Report on Patentability for PCT/EP2009/001989, dated Oct. 14, 2010.
International Search Report for PCT/EP2009/001985, mail dated Jun. 10, 2009.

(56) References Cited

OTHER PUBLICATIONS

Translation of International Preliminary Report on Patentability for PCT/EP2009/001985, dated Oct. 14, 2010.
International Search Report for PCT/EP2009/001986, mail dated Jun. 18, 2009.
Translation of International Preliminary Report on Patentability for PCT/EP2009/001986, dated Oct. 14, 2010.
International Search Report for PCT/EP2009/001987, mail dated Jun. 10, 2009.
Translation of International Preliminary Report on Patentability for PCT/EP2009/001987, dated Oct. 14, 2010.
International Search Report for PCT/EP2009/001984, mail dated Jun. 10, 2009.
Translation of International Preliminary Report on Patentability for PCT/EP2009/001984, dated Oct. 14, 2010.
International Search Report for PCT/EP2009/001990, mail dated Jun. 10, 2009.
Translation of International Preliminary Report on Patentability for PCT/EP2009/001990, dated Dec. 9, 2010.
International Search Report for PCT/EP2009/001988, mail dated Jul. 9, 2009.
Translation of International Preliminary Report on Patentability for PCT/EP2009/001988, dated Jan. 27, 2011.
International Search Report for PCT/EP2010/003446, mail dated Feb. 9, 2011.
Translation of International Preliminary Report on Patentability for PCT/EP2010/003446, dated Jan. 19, 2012.
International Search Report for PCT/EP2010/003447, mail dated Feb. 9, 2011.
Translation of International Preliminary Report on Patentability for PCT/EP2010/003447, dated Feb. 9, 2012.
Written Opinion of the IPEA for PCT/EP2010/003447, dated Sep. 9, 2011.
International Search Report for PCT/EP2010/003444, mail dated Feb. 9, 2011.
Translation of International Preliminary Report on Patentability for PCT/EP2010/003444, dated Jan. 19, 2012.
Response to the Written Opinion in PCT/EP2010/003444, dated Sep. 9, 2011.
International Search Report for PCT/EP2010/003445, mail dated Sep. 1, 2010.
Translation of International Preliminary Report on Patentability for PCT/EP2010/003445, dated Jan. 5, 2012.
International Search Report for PCT/EP2010/003442, mail dated Jul. 20, 2010.
Translation of International Preliminary Report on Patentability for PCT/EP2010/003442, dated Feb. 16, 2012.
International Search Report for PCT/EP2010/003443 mail dated Feb. 9, 2011.
Translation of International Preliminary Report on Patentability for PCT/EP2010/003443, dated Feb. 16, 2012.
International Search Report for PCT/EP2010/005427, dated Mar. 21, 2011.
Translation of International Preliminary Report on Patentability for PCT/EP2010/005427, dated Mar. 21, 2011.
International Search Report for PCT/EP2010/005428, dated Jan. 27, 2011.
Translation of International Preliminary Report on Patentability for PCT/EP2010/005428, dated Jan. 27, 2011.
International Search Report for PCT/EP2011/006173 mail dated May 8, 2012.
Translation of International Preliminary Report on Patentability for PCT/EP2011/006173, dated Jul. 4, 2013.
International Search Report for PCT/EP2011/006172 mail dated Jul. 10, 2012.
Translation of International Preliminary Report on Patentability for PCT/EP2011/006172, dated Jul. 4, 2013.
International Search Report for PCT/EP2011/006175, mail dated May 9, 2012.

Translation of International Preliminary Report on Patentability for PCT/EP2011/006175, dated Jul. 4, 2013.
International Search Report for PCT/EP2011/006174, mail dated Jul. 10, 2012.
Translation of International Preliminary Report on Patentability for PCT/EP2011/006174, dated Jul. 4, 2013.
International Search Report for PCT/EP2011/006176 mail dated Aug. 1, 2012.
Translation of International Preliminary Report on Patentability for PCT/EP2011/006176, dated Jul. 4, 2013.
"Microwave Synthesis" by B. L. Hayes, CEM Publishing 2002.
"Microwave vs. Conventional Heating", webpage, www.biotage.com, Jan. 2009.
Amore et al. (Macromolecular Rapid Communications, vol. 28 (2007), Issue 4, pp. 473-477).
An et al. (J. Org. Chem. (1997), 62, 2505-2511).
B. Toukoniitty, et al: "Esterification of propionic acid under microwave irradiation over an ion-exchange resin", Catalysis Today, Elsevier, NL, vol. 100, No. 3-4, Feb. 28, 2005, pp. 431-435, XP004850051.
Beilstein Substance Identification, BRN No. 6190607, 1981.
C. Ferroud, et al: "Microwaves-assisted solvent-free synthesis of N-acetamides by amidation or aminolysis", Tetrahedron Letters., vol. 49, Mar. 6, 2008. pp. 3004-3008, XP022602751 NL Elsevier, Amsterdam.
C. Chen et al., J. Chem. Soc., Chem. Commun., 1990, 807-809.
Chemat, et al: "The role of selective heating in the microwave activation of heterogeneous catalysis reactions using a continuous microwave reactor", Journal of Microwave Power and Electromagnetic Energy, The Institute, Vienna, VA, US, vol. 33, No. 2, Jan. 1, 1998, pp. 88-94 XP009143773.
D. Bogdal, Microwave-assisted Organic Synthesis, Elsevier 2005.
Energieeintrag im Discover, "Flexibilitaet ist Trurnpf", http://www.cem.de/documents/produlde/mikro_synthese/allgemeines/flexibel.htm, Jun. 2009.
English Abstract for DD 224203, Jul. 3, 1985.
English Abstract for EP 1291077, Mar. 12, 2003.
English Abstract for JP 52125142, Oct. 20, 1977.
English Abstract for JP 54005931, Jan. 17, 1979.
Erik Esveld, et al: "Pilot Scale Continuous Microwave Dry-Media Reactor. Part 1: Design and Modeling", Chemical Engineering and Technology, Weinheim, DE, vol. 23, No. 3, Jan. 1, 2000, pp. 279-283, XP007916923.
Erik Esveld, et al: "Pilot Scale Continuous Microwave Dry-Media Reactor Part II: Application to Waxy Esters Production", Chemical Engineering and Technology, Weinheim, DE, vol. 23, No. 5, Jan. 1, 2000, pp. 429-435, XP007916803.
G. Pipus, et al: "Esterification of benzoic acid in microwave tubular flow reactor", Chemical Engineering Journal, Elsevier Sequoia, Lausanne, CH, vol. 76, Jan. 1, 2000, pp. 239-245, XP007916929.
Gelens et al., Tetrahedron Letters 2005, 46(21), 3751-3754
Glasnov, et al: "Microwave-assisted synthesis under continuous-flow conditions", Macromolecular Rapid Communications, 28(4), 395-410 CODEN: MRCOE3; Jan. 1, 2007, XP00259633.
Goretzki et al., Macromol. Rapid Commun. 2004, 25, 513-516.
H.J. Bauer, et al., Makromol. Chem., 183, 1982, pp. 2971-2976.
Iannelli et al., Tetrahedron 2005, 61, 1509-1515.
J. Kremsner, et al, Top Curr Chem, (2006) 266: pp. 233-278.
J. Ruhoff. et al., J. Am. Chem. Soc., 59 (1937), 401-402.
K. Lange, K.H. Löcherer, Taschenbuch der Hochfrequenztechnik [Pocket book of high-frequency technology], vol. 2, p. K21 ff.
Katritzky et al. (Energy & Fuels 4 (1990), 556-561).
Konrad G. Kabza, et al: "Microwave-Induced Esterification Using Heterogeneous Acid Catalyst in a Low Dielectric Constant Medium", Journal of Organic Chemistry, American Chemical Society, Easton.; US, vol. 65, Jan. 1, 2000, pp. 1210-1214, XP007916930.
Kumar, et al., "Microwave Assisted Direct Synthesis of 2-Substituted Benzoxazoles From Carboxylic Acids Under Catalyst and Solvent-Free Conditions", Synlett, No. 9, 2005, pp. 1401-1404.
L. Perreux, et al: "Microwave effects in solvent-free esters aminolysis" Tetrahedron, Elsevier Science Publishers, Amsterdam, NL, vol. 59, No. 12, Mar. 17, 2003, pp. 2185-2189, XP004414169.

(56) References Cited

OTHER PUBLICATIONS

L. Perreux, et al: "Solvent-free preparation of amides from acids and primary amines under microwave irradiation", Tetrahedron, Elsevier Science Publishers, Amsterdam, NL, vol. 58, No. 11, Mar. 11, 2002, pp. 2155-2162, XP004343866.
M. S. Neiy, et al., "Niobium pentachloride promoted conversion of carboxylic acids to carhoxamides: Synthesis of the 4-aryl-1,2,3,4-tetrahydrolsoquinollne alkaloid structures" Synthesis, (2),272-276, 2003.
Massicot at al., Synthesis 2001 (16), 2441-2444.
Noel S. Wilson, et al: "Development and Applications of a Practical Continuous Flow Microwave Cell", Organic Process Research and Development, American Chemical Society, US, vol. 8, No. 3, Jan. 1, 2004, pp. 535-538, XP007916928.
Pipus et al. (First European Congress on Chemical Engineering, Firenze, Italy, May 4-7, 1997; AIDIC: Milan, Italy, 1997; pp. 45-48).
Q. Yang et al. (Synth. Commun. 2008, 38, 4107-4115).
R. Jachuck, et al: "Process intensification: oxidation of benzyl alcohol using a continuous isothermal reactor under microwave irradiation". Green Chemistry, Royal Society of Chemistry, Cambridge, GB, vol. 8, Jan. 1, 2006, pp. 29-33, XP007916789.
R. Martinez-Palou, et al., "Synthesis of Long Chain 2-Alkyl-1-(2-hydroxyethyl)-2-imidazolines Under Microwave in Solvent-Free Conditions", Synlett 2003, No. 12, pp. 1847-1849.
R. Plantier-Royon, et al., "Synthesis of Functionalized Bis-Amides of L-(+)-Tartaric Acid and Application as Copper(11) Ligands", C.R. Chimie, 2004, pp. 119-123.
R. S. Varma, et al: "Solvent-free synthesis of amides from non-enolizable esters and amines using microwave irradiation" Tetrahedron Letters, Elsevier, Amsterdam, NL, vol. 40, No. 34, Aug. 20, 1999, pp. 6177-6180, XP004174006.
R. S. Hunter, "Conversion of Visual to Instrumental Measurements of Yellowness", 1981, JAOCS, May, pp. 606-612.
S. Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.
Synthewave 402 Manual, 2000, Prolabo, Support pp. (2) and Manual pp. 1-13 (total 15 pages).
T. Cablewski, et al: "Development and Application of a Continuous Microwave Reactor for Organic Synthesis" Journal of Organic Chemistry, American Chemical Society, Easton.; US, vol. 59, Jan. 1, 1994, pp. 3408-3412, XP000198783.
Vazquez-Tato, M.P., "Microwave-Mediated Synthesis of Amides", Synlett, No. 7, 1993, p. 506.
X. Wu, et al., "Microwave Enhanced Aminocarbonylations in Water", Organic Letters, 7(15), pp. 3327-3329, 2005.
Zradni et al. (Synth. Commun. 2002, 32, 3525-3531).
"Objective Colour Assesment and Quality Control in the Chemical, Pharmaceutical and Cosmetic Industries", Application Report No. 3.9 e from Hach Lange, pp. 1-28, Feb. 2013.
(Hawley's Condensed Chemical Dictionary, 14th ed., Lewis, Richard J. Sr. ed., copyright 2002 John Wiley & Sons, Inc., available online at http://www.knovel.comiwebiportalibrowseidisplay?EXT Knovel Display bookid=704&VerticalID=0).
A. Breccia et al, "Reaction Between Methanol and Commercial Seed Oils Under Microwave Irradiation" Internation Microwave Power Institute 1999, 34, pp. 3-8.
Advanced Organic Chemistry: Reactions, Mechanisms, and Structure; Second Edition, Jerry March, Wiley-Interscience Publication, pp. 324-331 and 382-389, 1977.
Wolf, et al., AOSTRA Journal of Research 3 (1986) "Microwave Assisted Catalytic Conversion of Cyclohexene" pp. 53-59.
Arfan et al, "Efficient Combination of Recyclable Task Specific Ionic Liquid and Microwave Dielectric Heating for the Synthesis of Lipophilic Esters," Organic Process Research & Development vol. 9, pp. 743-748 (2005).
Arora et al, "A mild and efficient procedure for the conversion of aromatic carboxylic acid esters to secondary amides" Can. J. Chem, vol. 83 (2005), pp. 1137-1140.
Barbosa et al, "Niobium to alcohol mol ratio control of the concurring esterification and etherification reactions promoted by NbCI5 and A1203 catalysts under microwave irradiation," App. Catalysis A: General vol. 338, pp. 9-13 (2008).
Bose et al, "Microwave promoted energy-efficient N-formylation with aqueous formic acid," Tetrahedron Let. vol. 47 (2006), pp. 4605-4607.
C. Mazzocchia et al., "Fatty acid methyl esters synthesis from triglycerides over heterogeneous catalysts in the presence of microwaves" C.R. Chimie 7 (2004) pp. 601-605.
Desai et al, "Thermal and microwave-assisted N-formylation using solid-supported reagents," Tetrahedron Let. vol. 46 (2005), pp. 955-957.
DiLuca et al, "A new, simple procedure for the synthesis of formyl amides," Synlett No. 14 (2004), pp. 2570-257.
Ella Bezdushna et al, Macromolecular Chemistry & Physics, vol. 209, pp. 1942-1947, XP55023715, 2008.
Ella Bezdushna et al: "Microwave-Assisted Esterification of Methacrylic Acid and Polymer-Analogous Esterification of Poly[ethylene-co-(acrylic acid)] with Dissimilar Phenols", Macromolecular Rapid Communications, vol. 208, No. 4, Feb. 19, 2007, pp. 443-448, XP55023715.
English Abstract for CH 681586, Apr. 15, 1993.
English Abstract for CN 1749279, Mar. 2006.
English Abstract for CN 1931980. Mar. 2007.
English Abstract for DE 102005051637, May 3, 2007.
English Abstract for DE 102009001382, Sep. 9, 2010.
English Abstract for DE 2620638, Nov. 24, 1977.
English Abstract for DE 480866, Aug. 1928.
English Abstract for EP 0134995, Mar. 27, 1985.
English Abstract for EP 1256585, Nov. 13, 2002.
English Abstract for JP 10330333, May 1997.
English Abstract for JP 2003321427, Nov. 11, 2003.
English Abstract for JP 2005060256, Mar. 10, 2005.
English Abstract for JP 2005322582. May 2005.
English Abstract for JP 2006181533, Dec. 2004.
English Abstract for JP 2006272055, Mar. 2005.
English Abstract for JP 2008031082, Feb. 14, 2008.
English Abstract for WO 03/090669. Nov. 6, 2003.
English Translation of CN 1351954, Jun. 5, 2002.
English translation of DIN Standard 6162, Mar. 2013.
English translation of JP 2009 263 497, 2009.
Essen et al, "The Velocity of Propagation of Electromagnetic Waves Derived from the Resonant Frequencies of a Cylindrical Cavity Resonator," Proc. R. Soc. Lond. A (1948), vol. 194, pp. 348-361.
Fats and Oils: Formulating and Processing for Applications, Second Ed., O'Brien, CRC Press 2003, Ch. 3, sec. 3.4.2., lines 12-13.
Fatty Acids Division, Soap Association, "Fatty Acids for Chemical Specialties: A symposium of the Soap, Detergents, and Sanitary Chemical Products Division of the Chemical Specialties Manufacturers Association," 1955, pp. 131-147, available online at http://www.aciscience.org/Oleochemical/FattyAcid.espx.
Gonzalez et al, "Tanradiamide formation by thermolysis of tartaric acid with alkylamines," Tetrahedron Letters vol. 49 (2008 3925-3926.
Ishihara at al, "3,4,5-Trifluorabenzeneboronic Acid as an Extremely Active Amidation Catalyst," J. Org. Chem. vol. 61, (1996), pp. 4196-4197.
Jain et al, "Acetylation of some organic compounds under microwave irradiation," J. Indian Chem. Soc., vol. 84, Feb. 2007, p. 188.
Kangani, et al., "One Pot direct synthesis of amides or oxazolines from carboxylic acids using Deoxo-Fluor reagent," Tetrahedron Letters, vol. 46, (2005), pp. 8917-8920.
Karl G. Kempf et al: "A Procedure for Preparing Aryl Esters of Polyacids. The Conversion of Poly(methacrylic acid) to Poly(phenyl methacrylate)", Macromolecules, vol. 11, No. 5, Sep. 1, 1978, pp. 1038-1041, XP55024162.
Katritzky et al, "Efficient microwave access to polysubstituted amidines from imidoylbenzotriazoles," J. Org. Chem. vol. 71, pp. 3375-3380 (2006).

(56) References Cited

OTHER PUBLICATIONS

KIC Chemicals Inc., Capric Acid, available online at http://www.kicgroup.com/capric.htm.
Leadbeater, et al, Continuous-Flow Preparation of Biodiesel Using Microwave Heating:, Energy & Fuels 2007, 21, pp. 1777-1781.
M. Hajek in A. Loupe "Microwaves in Organic Synthesis", Wiley, 2006, Chapter 13, pp. 615-652.
Machetti, et al., "Parallel Synthesis of an Amide Library Based on the 6,8-Dioxa-3-azabicyclo[3.2.1.]octane Scaffold by Direct Aminolysis of Methyl Esters," J. Comb, Chem., 2007, vol. 9, pp. 454-461.
Mazzocchia, C., et al., Fast synthesis of biodiesel from trigycerides in presence of microwave, 2006, Advances in Microwave and Radio Frequency Processing, Report of the 8th international conference on microwave and high frequency heatting held in Bayrueth, Germany, Sep. 2001, Springer Berlin Heidelberg, Part V, pp. 370-376 (18 pages).
Mohan et al, "Zeolite catalyzed acylation of alcohols and amines with acetic acid under microwave irradiation," Green Chem. 2006, vol. 8, pp. 368-372.
N. Azcan et al, "Alkali catalyzed transesterification of cottonseed oil by microwave irradiation" Fuel 86 (2007) pp. 2639-2644, XP022322088.
N. Azcan et al, "Microwave assisted tranesterification of rapeseed oil" Fuel 87 (2008) pp. 1781-1788, XP022611169.
N. Leadbeater et al, "Fast, Easy Preparation of Biodiesel Using Microwave Heating" Energy & Fuels 2006, 20, pp. 2281-2283.
N. Saifuddin et al, "Production of Ethyl Ester (Biodiesel) from used Frying Oil: Optimization of Transesterification Process using Microwave Irradiation" Malaysian Journal of Chemistry, 2004, vol. 6, pp. 77-82.
Oliver Kretschmann et al: Microwave-Assisted Synthesis of Associative Hydrogels., Macromolecular Rapid Communications, vol. 28, No. 11, Jun. 1, 2007, pp. 1265-1269, XP55023774.
Petricci et al, "Microwave-assisted acylation of amines, alcohols, and phenols by the use of solid-supported reagents (SSRs)," J. Org. Chem. vol. 69, pp. 7880-7887, (2004).
Poliington, Journal of Organic Chemistry, vol. 56, pp. 1313-1314, 1991.
Reddy et al, "Zirconyl chloride promoted highly efficient solid phase synthesis of amide derivatives," Chinese Chemical Letters, vol. 18 (2007), pp. 1213-1217.
Sebastian Sinnwell et al: "Microwave assisted hydroxyalkylamidation of poly(ethylene-co-acrylic acid) and formation of grafted poly([epsilon]-caprolactone) side chains", J. of Polymer Science Part A: Polymer Chemistry, vol. 45, No. 16, Aug. 15, 2007, pp. 3659-3667.
Shore, at al, "Catalysis in Capillaries by Pd Thin Films Using Microwave-Assisted Continuous-Flow Organic Synthesis (MACOS)" Angewandte Chemie 2006, 118, pp. 2827-2832.
Translation of SIPO Office Action for Application 20090101830.0, May 12, 2012.
Translation of SIPO Search Report for Application 200980101830.0: May 12, 2012.
V. Lertsathapornsuk et al, "Microwave assisted in continous biodiesel production from waste frying palm oil and its performance in a 100 kW diesel generator" Fuel Processing Technology 89 (2008) pp. 1330-1336, XP025681095.
Vacek et al. "Selective enzymic esterification of free fatty acids with n-butanol under microwave irradiation and under classical heating," Biotechnology Letters, vol. 22, pp. 1565-1570 (2000).
Werner et al, "Design and synthesis of a 3,4-dehydroproline amide discovery library," J. Comb. Chem. (2007), 9(4), pp. 677-683.
Zhaoju Yu et al: "Biodegradable polyvinyl alcohol)-graftpoly(epsilon-caprolactone) comb-like polyester: Microwave synthesis and its characterization", Journal of Applied Polymer Science, vol. 104, No. 6, Jun. 15, 2007, pp. 3973-3979, XP65023817.
Zraini, et al, "Minutes Synthesis of Amides from Esters and Amines Under Microwave Irradiation," Fifth International Electronic Conference on Synthetic Organic Chemistry (ECSOC-5), available at http://www.mdpi.org/ecsoc/ecsoc-5/Papers/e0013/e0013.html.

USPTO Non-Final Rejection for U.S. Appl. No. 12/444,643, dated Apr. 27, 2011.
USPTO Non-Final Rejection for U.S. Appl. No. 12/444,643, dated Aug. 13, 2012.
USPTO Non-Final Rejection for U.S. Appl. No. 12/444,643, dated Dec. 6, 2013.
USPTO Final Rejection for U.S. Appl. No. 12/444,643, dated Sep. 15, 2011.
USPTO Final Rejection for U.S. Appl. No. 12/444,643, dated Feb. 14, 2013.
USPTO Final Rejection for U.S. Appl. No. 12/444,643, dated Jul. 2, 2014.
USPTO Non-Final Rejection for U.S. Appl. No. 12/444,655, dated Jan. 19, 2011.
USPTO Non-Final Rejection for U.S. Appl. No. 12/444,669, dated Apr. 8, 2011.
USPTO Final Rejection for U.S. Appl. No. 12/444,678, dated Feb. 28, 2012.
USPTO Non-Final Rejection for U.S. Appl. No. 12/444,678, dated Jul. 19, 2011.
USPTO Requirement for Restriction/Election for U.S. Appl. No. 12/444,678, dated Apr. 14, 2011.
USPTO Non-Final Rejection for U.S. Appl. No. 12/935,308, dated Feb. 14, 2013.
USPTO Non-Final Rejection for U.S. Appl. No. 12/935,308, dated Oct. 2, 2014.
USPTO Final Rejection for U.S. Appl. No. 12/935,308, dated Sep. 5, 2013.
USPTO Final Rejection for U.S. Appl. No. 12/935,308, dated Jul. 16, 2015.
USPTO Requirement for Restriction/Election for U.S. Appl. No. 12/935,308, dated Dec. 18, 2012.
USPTO Final Rejection for U.S. Appl. No. 12/935,319, dated Aug. 30, 2013.
USPTO Final Rejection for U.S. Appl. No. 12/935,319, dated Jan. 26, 2015.
USPTO Non-Final Rejection for U.S. Appl. No. 12/935,319, dated Mar. 13, 2013.
USPTO Non-Final Rejection for U.S. Appl. No. 12/935,319, dated Jun. 25, 2014.
USPTO Non-Final Rejection for U.S. Appl. No. 12/935,319, dated Jun. 3, 2015.
USPTO Requirement for Restriction/Election for U.S. Appl. No. 12/935,319, dated Nov. 19, 2012.
USPTO Final Rejection for U.S. Appl. No. 12/935,375, dated Jan. 23, 2015.
USPTO Final Rejection for U.S. Appl. No. 12/935,375, dated Aug. 28, 2013.
USPTO Non-Final Rejection for U.S. Appl. No. 12/935,375, dated Jun. 19, 2014.
USPTO Non-Final Rejection for U.S. Appl. No. 12/935,375, dated Feb. 21, 2013.
USPTO Requirement for Restriction/Election for U.S. Appl. No. 12/935,375, dated Nov. 19, 2012.
USPTO Non-Final Rejection for U.S. Appl. No. 12/935,628, dated Jun. 26, 2013.
USPTO Final Rejection for U.S. Appl. No. 12/935,661, dated Jan. 26, 2015.
USPTO Final Rejection for U.S. Appl. No. 12/935,661, dated Aug. 28, 2013.
USPTO Non-Final Rejection for U.S. Appl. No. 12/935,661, dated Jul. 8, 2014.
USPTO Non-Final Rejection for U.S. Appl. No. 12/935,661, dated Feb. 14, 2013.
USPTO Requirement for Restriction/Election for U.S. Appl. No. 12/935,661, dated Oct. 24, 2012.
USPTO Final Rejection for U.S. Appl. No. 12/935,683, dated Jan. 22, 2015.
USPTO Final Rejection for U.S. Appl. No. 12/935,683, dated Aug. 29, 2013.
USPTO Non-Final Rejection for U.S. Appl. No. 12/935,683, dated Jul. 8, 2014.
English Abstract for JP 2000-351853, 2000.

(56) References Cited

OTHER PUBLICATIONS

USPTO Non-Final Rejection for U.S. Appl. No. 12/935,683, dated Feb. 14, 2013.
USPTO Requirement for Restriction/Election for U.S. Appl. No. 12/935,683, dated Dec. 17, 2012.
USPTO Final Rejection for U.S. Appl. No. 12/935,720, dated Jun. 18, 2014.
USPTO Non-Final Rejection for U.S. Appl. No. 12/935,720, dated Apr. 8, 2015.
USPTO Non-Final Rejection for U.S. Appl. No. 12/935,720, dated Sep. 5, 2013.
USPTO Non-Final Rejection for U.S. Appl. No. 12/935,720, dated Mar. 19, 2013.
USPTO Requirement for Restriction/Election for U.S. Appl. No. 12/935,720, dated Dec. 17, 2012.
USPTO Final Rejection for U.S. Appl. No. 13/378,151, dated Sep. 8, 2014.
USPTO Non-Final Rejection for U.S. Appl. No. 13/378,151, dated Jun. 2, 2015.
USPTO Non-Final Rejection for U.S. Appl. No. 13/378,151, dated Dec. 18, 2013.
USPTO Requirement for Restriction/Election for U.S. Appl. No. 13/378,151, dated Sep. 30, 2013.
USPTO Final Rejection for U.S. Appl. No. 13/378,167, dated Jun. 4, 2015.
USPTO Non-Final Rejection for U.S. Appl. No. 13/378,167, dated Sep. 8, 2014.
USPTO Non-Final Rejection for U.S. Appl. No. 13/378,167, dated Dec. 18, 2013.
USPTO Requirement for Restriction/Election for U.S. Appl. No. 13/378,167, dated Oct. 1, 2013.
USPTO Final Rejection for U.S. Appl. No. 13/378,181, dated Jun. 3, 2015.
USPTO Non-Final Rejection for U.S. Appl. No. 13/378,181, dated Sep. 9, 2014.
USPTO Non-Final Rejection for U.S. Appl. No. 13/378,181, dated Dec. 18, 2013.
USPTO Requirement for Restriction/Election for U.S. Appl. No. 13/378,181, dated Oct. 1, 2013.
USPTO Final Rejection for U.S. Appl. No. 13/378,226, dated Sep. 10, 2014.
USPTO Non-Final Rejection for U.S. Appl. No. 13/378,226, dated Jun. 2, 2015.
USPTO Non-Final Rejection for U.S. Appl. No. 13/378,226, dated Dec. 27, 2013.
USPTO Requirement for Restriction/Election for U.S. Appl. No. 13/378,226, dated Oct. 1, 2013.
USPTO Final Rejection for U.S. Appl. No. 13/378,242, dated Sep. 23, 2014.
USPTO Non-Final Rejection for U.S. Appl. No. 13/378,242, dated Jun. 3, 2015.
USPTO Non-Final Rejection for U.S. Appl. No. 13/378,242, dated Dec. 31, 2013.
USPTO Requirement for Restriction/Election for U.S. Appl. No. 13/378,242, dated Oct. 1, 2013.
USPTO Non-Final Rejection for U.S. Appl. No. 13/378,258, dated Jul. 19, 2013.
USPTO Non-Final Rejection for U.S. Appl. No. 13/497,429, dated Mar. 20, 2014.
USPTO Final Rejection for U.S. Appl. No. 13/976,709, dated Aug. 28, 2015.
USPTO Final Rejection for U.S. Appl. No. 13/976,709, dated Oct. 10, 2014.
USPTO Non-Final Rejection for U.S. Appl. No. 13/976,709, dated Mar. 20, 2015.
USPTO Non-Final Rejection for U.S. Appl. No. 13/976,709, dated May 20, 2014.
USPTO Non-Final Rejection for U.S. Appl. No. 13/977,346, dated Jan. 14, 2015.
USPTO Non-Final Rejection for U.S. Appl. No. 13/977,468, dated Feb. 6, 2015.
English Abstract for JP 2005-002284, 2005.
English Abstract for JP 2010-207735, 2010.

\* cited by examiner

APPARATUS FOR CONTINUOUSLY CARRYING OUT HETEROGENEOUSLY CATALYZED CHEMICAL REACTIONS AT ELEVATED TEMPERATURES

The present invention relates to an apparatus for continuous performance of heterogeneously catalyzed chemical reactions at high temperatures and elevated pressure under microwave irradiation on the industrial scale.

Chemical reactions can be accelerated by catalysts. Reactions of particular interest are heterogeneously catalyzed reactions in which the reaction mixture flows past an immobilized, catalytically active material. In contrast to homogeneously catalyzed reactions, essentially no residues remain in the product thus produced and, with appropriate design of the apparatus, large product volumes can be produced in high space-time yields. Catalyzed reactions are particularly efficient when they are performed at high temperatures, though the temperatures required for the performance of these reactions are still lower than without presence of the catalyst.

Typically, continuous, heterogeneously catalyzed reactions are performed in reactors which comprise catalytically active solids or support materials impregnated with catalytically active species, through which the reaction mixture flows. A problem for the performance of heterogeneously catalyzed reactions on the industrial scale is often the homogeneous establishment of the temperatures in the reaction mixture required for the activation of the reactions over the entire cross section of the reactor. The higher jacket temperatures or else heating element temperatures needed to ensure the required heat transfer frequently lead, at the heating surfaces, to local (partial) overheating of the reaction mixture and, as a result of this, in many cases to unwanted side reactions or else decompositions of the reaction mixture, which reduces product quality and/or yield. In technical terms, limits are additionally placed on the temperature increase by the pressures which then occur. At least in large reaction vessels of several liters or several cubic meters, the performance of reactions under high pressures is achievable only with a high level of technical complexity, if at all, due to the safety risks which then arise. Furthermore, the random solid packings typically used as catalysts lead to a high pressure drop in the reactor due to their low porosity.

In order to perform continuous reactions at high temperatures and high pressures on the industrial scale, it is customary to use flow-operated thick-wall vessels or long tubes with low cross section (flow tubes), in order firstly to satisfy the safety demands and secondly to ensure the residence times required to achieve yields of interest. For such processes, the establishment of the high heating rates required requires jacket temperatures which rise with scale, and which, as already stated, can lead to unwanted side reactions or else decomposition. Moderate jacket temperatures, in contrast, require long residence times in tanks to attain the target temperature, in which case the conversion is limited by the backmixing which then occurs; in flow tubes, low temperature gradients require either low flow rates and/or long tubes. During this slow heating, however, likewise unwanted side reactions, for example those promoted kinetically, are observed in many reactions.

A more recent approach to chemical synthesis is the performance of reactions in a microwave field. For instance, M. Hájek (in A. Loupy, Microwaves in Organic Synthesis, Wiley 2006, chapter 13) refers to a multitude of heterogeneously catalyzed reactions whose reaction rate and/or selectivity is enhanced by heating with microwaves. This reaction technique has to date been employed principally on laboratory scale and only rarely on the pilot plant scale, since there have been no known apparatuses to date which enable the production of more than a few kilograms per day and hence synthesis on the industrial scale.

Wolf et al. (AOSTRA J. of Research (1986) 3, 53) disclose flow apparatuses in which reactions catalyzed by nickel powder or nickel-containing alloys are performed under microwave irradiation. The apparatuses are designed for conversions on laboratory scale and cannot be enlarged to a scale of interest for industrial applications at least due to the limited penetration depth of microwaves.

Shore et al. (Angew. Chem. 2006, 118, 2827-2832) disclose capillaries which have been coated with palladium films and have a diameter of 1150 µm, in which microwave-supported reactions are performed. The palladium coating achieves distinctly increased conversions.

WO 2009/064501 discloses processes for catalytic desulfurization of crude oils under microwave irradiation. The apparatus design proposed, however, cannot be converted to an industrial scale at least due to the limitation in penetration depth of microwaves into material to a few centimeters.

WO 2006/024167 discloses a microreactor in which the reaction mixture flowing through a capillary comprising bodies coated with catalytically active substances or catalytically active bodies is exposed to microwave radiation which is injected at right angles to the longitudinal axis of the capillary. Due to the short irradiation zone and the penetration depth of microwaves into the reaction mixture of only a few centimeters, such apparatuses are restricted to operations on the laboratory scale.

Mazzocchia et al. (C. R. Chemie, 2004, 7, 601-605) disclose microwave-supported transesterifications of triglycerides with methanol under heterogeneous catalysis by zeolites. This achieves only moderate conversions at 170° C. with irradiation for two hours in a closed vessel.

Esveld et al. (Chem. Eng. Technol. 23 (2000), 429-435) disclose a continuous process for preparing wax esters, in which fatty alcohol and fatty acid are esterified without solvent in the presence of montmorillonite. On a conveyor belt, the reaction mixture is heated to reaction temperature by microwave radiation within 5 minutes and then kept at this temperature for a further 30 minutes for substantial removal of the water of reaction which forms. This process is of course applicable only to high-boiling reactants (and reaction products).

It was accordingly an object of the invention to provide an apparatus for continuous performance of heterogeneously catalyzed chemical reactions on the industrial scale at high temperatures, in which the reaction mixture can be heated to the desired reaction temperature very rapidly and without partial overheating. In addition, the apparatus should enable operation above atmospheric pressure, such that the reaction mixture remains in the liquid or dissolved state even at elevated temperatures. The apparatus should enable a high space-time yield, a high energy efficiency and additionally safe and reproducible operation. It was a further object of the invention to provide an apparatus for continuous performance of microwave-supported reactions, in which inhomogeneous reaction mixtures and/or immiscible or incompletely miscible reactants can be exposed to the microwave irradiation with vigorous mixing.

It has been found that, surprisingly, heterogeneously catalyzed chemical reactions can be performed in a continuous process in volumes of industrial relevance in an apparatus in which the reaction mixture to be converted is heated by irradiation with microwaves in a microwave-transparent tube whose longitudinal axis is in the direction of propagation of the microwaves from a monomode microwave applicator, the microwave-transparent tube being filled with an open-cell foam which is catalytically active and/or bears catalytically active species. In the inventive apparatus, the foam which is catalytically active and/or bears catalytically active species and the reaction mixture which flows through it are heated homogeneously, and there is no significant temperature gradient between the interior of the open-pore foam which is catalytically active and/or bears catalytically active species and the tube wall surrounding it. This apparatus allows very rapid but nevertheless gentle heating of the reaction mixture with very high space-time yields and high energy efficiency. Furthermore, the rate of heating and the maximum temperature can be established simply, rapidly and reproducibly by regulation of the incident microwave power. Furthermore, very vigorous mixing of the reaction mixture takes place during the microwave irradiation.

Figure 1:
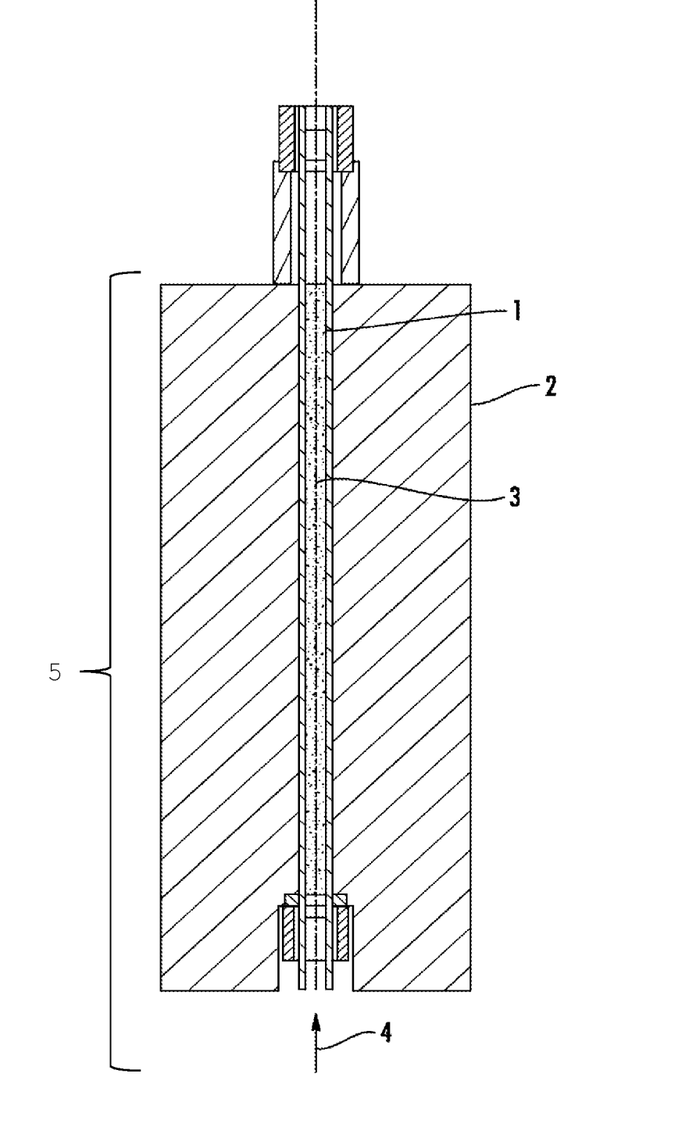
FIG. 1 is a perspective view of a preferred embodiment of the present invention.

Referring to the drawings, FIG. 1 is a view from the side of an apparatus for continuous performance of heterogeneously catalyzed chemical reactions, as described by one embodiment of the present invention. The four basic components of the apparatus are visible. A monomode microwave applicator 5 includes a hollow conductor 2 and a source of microwaves 4. A substantially microwave-transparent reaction tube 1 is disposed within the hollow conductor, with its longitudinal axis is in a direction of propagation of the microwaves 4 from the monomode microwave applicator 5. The microwave-transparent tube is filled with an open-cell foam 3.

The invention provides an apparatus for continuous performance of heterogeneously catalyzed chemical reactions, comprising a microwave-transparent tube whose longitudinal axis is in the direction of propagation of the microwaves from a monomode microwave applicator, the microwave-transparent tube being filled with an open-cell foam bearing or consisting of catalytically active species.

The invention further provides a process for performing heterogeneously catalyzed chemical reactions, in which the reaction mixture is converted by irradiation with microwaves in a microwave-transparent tube whose longitudinal axis is in the direction of propagation of the microwaves from a monomode microwave applicator, the microwave-transparent tube being filled with an open-cell foam bearing or consisting of catalytically active species.

Inventive apparatus and inventive process are preferentially suitable for reactions in organic chemistry. They are especially suitable for those reactions whose reaction rate can be accelerated by the presence of catalytically active species. Acceleration of the reaction rate is understood to mean here that, under otherwise identical reaction conditions, for example temperature and pressure, there is more conversion per unit time than without presence of the catalyst and/or that the presence of the catalyst, for the same conversion, enables increased throughput. They are additionally preferred for reactions which proceed without significant exothermicity. For instance, inventive apparatus and the process performed therein are suitable especially for the performance of reactions whose heat of reaction $\Delta H$ is less than $-50$ kJ/mol and especially less than $-20$ kJ/mol, for example less than $-10$ kJ/mol. They are particularly preferred for endothermic reactions whose heat of reaction $\Delta H$ is greater than $+0.1$ kJ/mol and especially between $+1$ kJ/mol and $+250$ kJ/mol, for example between $+2$ kJ/mol and $+100$ kJ/mol. Since the cata-lytically active species typically exhibit a very high microwave absorption, it is also possible by the process according to the invention to react substances or reaction mixtures which themselves exhibit only very low microwave absorption. Examples of suitable chemical reactions are esterifications, transesterifications, amidations, ester hydrolyses, etherifications, acetalizations, ene reactions, Diels-Alder reactions, oxidations, ammoxidations, cyanizations, reductions, hydrogenations, hydrodeoxygenations, reductive aminations, nucleophilic substitutions, additions, hydrolyses, isomerizations, rearrangements, condensations, decarboxylations, eliminations, cyclizations, metathesis reactions, metal-catalyzed coupling reactions, for example Suzuki reactions, Heck couplings, Sonogashira couplings, Stille couplings, Ullmann reactions and Kumada couplings, alkylations, acylations, for example Friedel-Crafts acylations, cracking reactions and polymerizations, for example polycondensations. Inventive apparatus and process are also very suitable for the hydrogenating desulfurization of crude oils and mineral oil distillates. As well as the actual reactants, the reaction mixtures may also comprise assistants, for example solvents.

Open-cell foams are understood in accordance with the invention to mean materials with cellular structure and low density, in which the cell walls are essentially discontinuous. The foams thus consist preferably of cell walls joined to one another. Cell walls and cells form two continuous networks which penetrate one another. The open-pore foam consequently comprises a multitude of flow paths within a solid structure with a surface which is catalytically active or comprises catalytically active species.

The open-cell foam is preferably structured such that it enables flow of the reaction mixture in the longitudinal and transverse directions of the microwave-transparent tube, also referred to hereinafter as reaction tube. It is additionally structured such that it causes a minimum pressure drop in the reaction tube even at high flow rates. The pressure drop caused by the open-cell foam is preferably less than $5 \cdot 10^5$ Pa/m, more preferably less than $2 \cdot 10^5$ Pa/m and especially less than $1 \cdot 10^5$ Pa/m, for example less than $0.5 \cdot 10^5$ Pa/m, against air at a flow rate of 5 m/s. The porosity of preferred open-cell foams is at least 20%, preferably 35 to 99%, more preferably 50 to 95%, for example 70 to 90%. Porosity of the foam is understood to mean the ratio of density of the open-cell foam ($\rho$) to the density of the material which forms the cell walls ($\rho_s$):

$$\text{Porosity} = (1 - \rho/\rho_s) \cdot 100$$

Preferably, the open porosity is at least 50%, more preferably 65 to 100% and especially 70 to 99%, for example 75 to 95%, of the cells present overall. The pore count or cell size, which can be determined on the basis of ASTM D3576, may vary within wide limits. It is preferably 1 to 150 ppi (ppi=pores per inch), more preferably between 5 and 100 ppi and especially between 10 and 80, for example between 20 and 60, ppi. The pore size of preferred open-cell foams is between 1 cm and 0.01 mm and more preferably between 0.5 cm and 0.1 mm. Open-cell foams suitable in accordance with the invention have a strength which is at least sufficient to withstand the pressure of the reaction mixture which flows through it. Preferred open-cell foams have an average strength (breaking load), which can be determined by means of die indentation, of at least 100 N and especially of 200 to 15 000 N, for example of 300 to 10 000 N. The strength of foam ceramics can be determined with the aid of a simple test method, in which a test die with a defined diameter is indented into the foam ceramic and the force-distance curve is recorded. The force required to destroy the structure is assumed to be a measure of strength. It is reported as breaking load in the unit N and is determined as the mean from a pack of 10 samples. For instance, the strength of open-cell foams can be determined with a test machine which uses a test die with a diameter of 20 mm, and the specimen should measure at least 40×40 mm at right angles to the breaking load and should be at least 10 mm thick. The breaking load used is the first peak of the force-distance curve. This results from the fracture of the uppermost cell wall plane.

In a further preferred embodiment, the open-cell foam is shaped such that turbulent flow is imparted to the reaction mixture.

In a preferred embodiment, the microwave-transparent tube is filled with an open-cell foam with catalytically active surface area of specific shape, or comprises random packings formed from such an open-cell foam. In a particularly preferred embodiment, the open-cell foams constitute a surface for coating with or for intercalation of catalytically active species.

The dimensions of the open-cell foam are preferably such that it essentially fills the cavity of the reaction tube at least in the region (heating zone) exposed to the microwave radiation. More preferably, the foam has a geometry corresponding to the interior of the reaction tube and is fixed therein as a core. The diameter of such foam cores is preferably at least 90%, more preferably 95 to 99.9%, for example 96 to 99%, of the internal diameter of the reaction tube. In a particularly preferred embodiment, the foam core concludes flush with the wall of the reaction tube. This prevents the formation of channels in which the reaction mixture can flow through the reaction tube without passing through the open-cell foam which is catalytically active and/or bears catalytically active species. In a specific embodiment, reaction tube and foam are integrally joined to one another.

In a further embodiment, the open-cell foam can also be introduced into the reaction tube in the form of shaped bodies which are catalytically active and/or have been impregnated with catalytically active species. Suitable shaped bodies are any shapes, preference being given to tablets, rings, cylinders, stars, wagon wheels or spheres, particular preference being given to cylinders with a diameter corresponding to the cross section of the reaction tube. The volume of the reaction tube is preferably very substantially filled by the bed of shaped bodies. In this embodiment, preferably more than 50% by volume, more preferably 70 to 100% by volume, especially 80 to 99% by volume, for example 85 to 95% by volume, of the reaction tube has been filled with shaped bodies (including the pore volume). The random packings are preferably kept within the reaction tube by sieves, frits or constrictions in the cross section.

Preferably, the materials used for the production of open-pore foams have melting points above the target reaction temperature, more preferably at least 50° C. above the target reaction temperature, especially at least 100° C. and particularly at least 200° C. above the target reaction temperature.

In a first preferred embodiment, i), the open-cell foam is formed from ceramic material. Ceramic materials have a marked catalytic effect on many reactions. For use in reactions in which the ceramic material itself, however, exhibits only a very low catalytic activity, if any, the ceramic, in a second preferred embodiment ii), may be permeated or impregnated with one or more further catalytically active species. In a third preferred embodiment iii), the open-cell foam is formed essentially from one or more metals, especially transition metals, alloys comprising transition metals, oxides thereof or mixtures thereof.

Preferred ceramic foams of the first embodiment i) may consist of the same material as or a different material than the reaction tube. In a preferred embodiment i), the foam consists of the same material as the reaction tube. Preferred materials for ceramics suitable in accordance with the invention are, for example, aluminum oxide, sapphire, zirconium oxide, silicon nitride and the like, and mixtures thereof. Also suitable are silicon dioxide, silicates and especially quartz, and mixtures thereof with the aforementioned ceramics.

Open-pore ceramic foams are known in the prior art. Such ceramic foams are generally produced by firstly impregnating a foam structure which can be burnt off, typically an organic foam structure, for example a polyurethane foam, with a typically aqueous suspension (slip) comprising constituents for formation of a ceramic. Thereafter, the impregnated foam structure is optionally freed of excess suspension, dried to remove solvent and then calcined at a temperature at which the foam structure burns and the constituents of the suspension deposited on the foam structure sinter together to form a ceramic. This gives what is called a positive impression of the foam structure with the same macrostructure as possessed by the original polymer foam. More particularly, to achieve open-pore foams of particular mechanical stability, it has been found to be useful to fill the cavities of a polymeric foam with suspension comprising to form a ceramic, and then obtain what is called a negative impression of the polymer structure by pyrolytic removal of the original polymer. By variation, for example, in the polymeric substrate, in the coating density of the substrate, in the chemical composition of the suspension and/or in the process steps employed, it is possible to obtain a multitude of different open-cell structures. For example, it is possible to produce foams with different geometries, physical properties, porosities, flow resistances, specific surface areas, catalytic activities and/or lifetimes. For example, it is possible through suitable selection of polymer substrate, the composition of the slip and the sintering conditions to structure the open-cell foam in terms of macro-, meso- and/or microporosity such that it has a maximum surface area accessible to the reaction mixture in relation to the intrinsic volume.

"Macropores" are understood to mean pores with diameters of greater than about 500 ångström (Å), "mesopores" to mean pores with diameters of about 20 ångström to about 500 ångström, and "micropores" to mean pores with diameters of less than about 20 ångström.

A further example of a method for production of open-cell foams suitable in accordance with the invention is that of heterocoagulation. In this method, electrostatic interaction in colloidal systems, for example of nanoparticles suitable for formation of ceramic with polymer particles, gives structures which, after filtration and calcination, give rise to open-cell foams with properties suitable in accordance with the invention. Here too, by variation in, for example, size, shape, charge, charge density and chemical composition of nanoparticles, and also polymer particles, it is possible to adjust the properties of the resulting open-cell foams within wide limits. This method is especially suitable for production of open-cell ceramic foams with large surface area, high catalytic activity and low flow resistance.

Suitable open-cell foams also include structures which have been formed from aggregates of spheres, microspheres, grains, nanotubes and/or hollow fibers and have been consolidated by calcination, which have a large surface area and a multitude of flow paths. It is also possible by direct foaming of suspensions of ceramic-forming materials or of transition metals, or oxides, silicates, salts and/or complexes thereof, and optional calcination of the resulting structures, to obtain inventive open-cell foams.

For reactions in which the ceramic itself exhibits too low a catalytic activity, if any, it has been found to be useful, in a second preferred embodiment ii), to permeate, coat or impregnate the open-cell ceramics of the first preferred embodiment i) with one or more further catalytically active species. Thus, the open-pore foam, in a particularly preferred embodiment ii), consists of ceramic material into which catalytically active species have been intercalated and/or which has been coated or impregnated with catalytically active species.

Suitable catalytically active species are in principle all solid compounds which are capable of accelerating one or more chemical reactions without being consumed themselves. Catalysts preferred in accordance with the invention exhibit marked absorption of microwave radiation.

For example, the open-cell ceramic foam may be permeated by at least one acidic or basic material. Such foams are in principle obtainable by the same processes as the open-cell ceramic foams described above for embodiment i), by adding to the suspension comprising for formation of a ceramic catalytically active species or precursors thereof which are intercalated into the ceramic-forming composition.

Examples of such basic additives are, for example, salts and oxides of the alkali metals and alkaline earth metals, such as CaO, MgO, $Na_2O$, $K_2O$, $Na_2CO_3$, $K_2CO_3$, $Cs_2CO_3$ and mixtures thereof. It is also possible to add montmorillonite, zeolite, clay, silicates, aluminum oxide in acidic or basic form to the slip as catalytically active species. It is also possible to add boron carbide $B_4C$ to the slip. It is equally possible, for example, for open-cell ceramic foams obtainable by the processes described for embodiment i) to be coated or impregnated with these or other acidic or basic materials, for example by application of a solution or suspension of at least one catalytically active material and/or precursor thereof to the open-cell ceramic foam and subsequent drying and optional calcination of the foam thus treated.

In addition, the open-cell ceramic foam may be permeated or coated or impregnated with at least one transition metal, or oxide, sulfide, silicate, salt and/or complex thereof, transition metal-containing alloys and/or mixtures thereof. Particularly suitable transition metals are the elements of groups IVA to VIIIA and IA and IIA of the Periodic Table. Examples of catalytically active species suitable in accordance with the invention are transition metals and the oxides and silicates thereof. Examples of suitable metals are palladium, nickel, cobalt, platinum, rhodium, iron, copper, chromium, zinc, ruthenium, osmium, iridium, silver, gold, vanadium, tungsten, titanium, manganese, molybdenum, zirconium and aluminum, and the mixtures thereof. It is also possible in accordance with the invention to use mixtures and alloys of different metals, for example of different transition metals or of transition metals with main group metals, for example alkali metals and alkaline earth metals, as the catalyst. Examples of such mixtures are copper-zinc, nickel-molybdenum, cobalt-nickel-molybdenum, cobalt-molybdenum, nickel-tungsten, nickel-sodium and nickel-tungsten-titanium. Examples of suitable salts are acetates, halides, carbonates, nitrates, phosphates and/or sulfates; examples of ligands of complexes suitable in accordance with the invention are mono- and polydentate, for example bi-, tri- and polydentate, ligands, for example triphenylphosphine (TPP), dibenzylideneacetone, 1,2-bis(dicyclohexylphosphino)ethane, cyclopentadienyl; 2,3-bis(diphenylphosphino)bicyclo[2.2.1]hept-5-ene (NorPhos), bicyclo[2.2.1]hepta-2,5-diene (=Norbornadiene, NOR), 2,2'-bis[(N,N-dimethylamino)(phenyl)methyl]-1,1'-bisdicyclohexylphosphino)ferrocene (MandyPhos), 3,5-dioxa-4-phosphacyclohepta[2,1-a;3,4-a']dinapthalen-4-yl)dimethylarnine (MonoPhos), 4,4'-di-tert-butyl-4,4',5,5'-tetrahydro-3,3'-bis-3H-dinaphtho[2,1-c:1',2'-e]phosphepine (binapin), butoxycarbonyl-4-diphenylphosphino-2-diphenylphosphinomethylpyrrolidine (BPPM), (1R,2R)-bis[(2-methoxyphenyl)phenylphosphino]ethane (DIPAMP), O-isopropylidene-2,3-dihydroxy-1,4-bis(diphenylphosphino)butane (DIOP), 1,4-diazabicyclo[2.2.2]octane (DABCO), ethylenediaminetetraacetate (EDTA), tetramethylethylenediamine (TEMEDA), ethylenediamine (EN), diethylenetriamine (DIEN), iminodiacetate (IDA), diethylenetetraamine, triaminotriethylamine, nitrilotriacetate (NTA), ethylenediaminotriacetate (TED), diethylenetriaminepentaacetate (DTPA), 1,4,7,10-tetraazacyclododecane-1,4,7,10-tetraacetate (DOTA), oxalate (OX), citrate, tartrate, dimethylglyoxime (DMG), tris(pyrazolyl)borate (Tp), 2,2'-binaphtyldiphenyldiphosphine (BINAP), 8-hydroxyquinoline, 2,2'-bipyridine (BPY), 1,10-phenanthroline (PHEN), dimercaptosuccinic acid, nitrilotriacetic acid (NTA), and ligands based on the porphyrin framework.

The coating or impregnation of the open-pore ceramic foams can be effected, for example, by impregnating the ceramic with solutions or suspensions of transition metals, or salts and/or complexes thereof, to apply a layer of finely divided metal or metal salt and/or metal complex. The impregnation is preferably effected with soluble salts and/or complexes of abovementioned metals, for example the acetates, halides, nitrates, carbonates, phosphates and/or sulfates. As well as water, preference is given to polar organic solvents and mixtures of water and one or more polar organic solvents for preparation of the solutions and/or suspensions. The transition metals, and also the salts and complexes thereof, can be fixed on the open-cell foam, for example, by absorption, and especially complexes by chemical bonding. They can also be converted to the corresponding oxides of the metals by, for example, calcination or other chemical operations. In a particularly preferred embodiment, it is especially possible to coat the positive impression of a polymer foam with catalytically active species. The resulting structures can subsequently be optimized further, for example by sintering. The coating of the open-cell foams with catalytically active species can also be effected, for example, by powder coating, galvanization or vapor deposition.

Open-cell foams permeated and/or coated with catalytically active species contain preferably 0.001 to 25% by weight and more preferably 0.05 to 20% by weight, for example 0.1 to 10% by weight, of catalytically active species based on the total weight of the foam.

The open-cell foams of the third preferred embodiment iii) are formed essentially from one or more transition metals, alloys comprising transition metals, or the oxides, sulfides, silicates or mixtures thereof. Preferred catalytically active materials are transition metals and the oxides thereof. Particularly suitable transition metals are the elements of groups IVA to VIIIA and IA and IIA of the Periodic Table. Examples of suitable metals are palladium, nickel, cobalt, platinum, rhodium, iron, copper, chromium, zinc, ruthenium, osmium, iridium, silver, gold, vanadium, tungsten, titanium, manganese, molybdenum, zirconium and aluminum, and the mixtures thereof. It is also possible in accordance with the invention to use mixtures and alloys of different metals, for example of different transition metals or of transition metals with main group metals, for example alkali metals and alkaline earth metals, as the catalyst. Examples of such mixtures are copper-zinc, nickel-molybdenum, cobalt-nickel-molybdenum, cobalt-molybdenum, nickel-tungsten, nickel-sodium and nickel-tungsten-titanium.

The production of such foams can be effected in analogy to the processes described for the production of the ceramic foams of the first embodiment i). In this case, for example, a polymer foam is impregnated with the solution or suspension of one or more transition metals, alloys comprising transition metals, or the oxides, sulfides, salts and/or complexes thereof, and, after removal of excess material and drying, the polymer is removed pyrolytically. The polymer foam is preferably impregnated with soluble salts and/or complexes of above-mentioned metals, for example the acetates, halides, nitrates, carbonates, phosphates and/or sulfates. As well as water, polar organic solvents and mixtures of water and one or more polar organic solvents are preferred for preparation of the solutions and/or suspensions. It is possible to produce either positive or negative impressions of the polymer foam. Numerous further methods are known for production of open-cell foams suitable in accordance with the invention, for example the direct foaming of catalytically active metals or metal oxides.

It has often been found to be useful to activate the open-pore foam which is catalytically active or bears catalytically active species before use thereof. This can be accomplished, for example, by thermal treatment of the foam. A particularly useful method has been found to be thermal treatment under irradiation by microwaves. Metals or metal oxides can be converted to the sulfides in a known manner before they are used, for example, in hydrogenating desulfurization.

Microwaves refer to electromagnetic rays with a wavelength between about 1 cm and 1 m and frequencies between about 300 MHz and 30 GHz. This frequency range is suitable in principle for the process according to the invention. Preference is given in accordance with the invention to using microwave radiation with the frequencies approved for industrial, scientific, medical, domestic or similar applications, for example frequencies of 915 MHz, 2.45 GHz, 5.8 GHz or 24.12 GHz.

In a preferred embodiment, the microwave-transparent tube of the inventive apparatus is a pressure-resistant, chemically inert tube (reaction tube), in the course of flow through which the reaction mixture is exposed to microwave radiation. The reaction tube is essentially straight. The reaction mixture is preferably heated in a microwave-transparent, straight tube whose longitudinal axis is in the direction of propagation of the microwaves from a monomode microwave applicator.

The reaction mixture is preferably irradiated with microwaves in a microwave-transparent, straight reaction tube within a hollow conductor connected to a microwave generator. The reaction tube is preferably aligned axially with the central axis of symmetry of the hollow conductor.

The hollow conductor which functions as the microwave applicator is preferably configured as a cavity resonator. The length of the cavity resonator is preferably such that a standing wave forms therein. Additionally preferably, the microwaves unabsorbed by the reaction mixture in the hollow conductor are reflected at the end thereof. Configuration of the microwave applicator as a resonator of the reflection type achieves a local increase in the electrical field strength at the same power supplied by the generator and increased energy exploitation.

The cavity resonator is preferably operated in $E_{01n}$ mode where n is an integer and specifies the number of field maxima of the microwave along the central axis of symmetry of the resonator. In this operation, the electrical field is directed in the direction of the central axis of symmetry of the cavity resonator. It has a maximum in the region of the central axis of symmetry and decreases to the value 0 toward the outer surface. This field configuration is rotationally symmetric about the central axis of symmetry. Use of a cavity resonator with a length where n is an integer enables the formation of a standing wave. According to the desired flow rate of the reaction mixture through the reaction tube, the temperature required and the residence time required in the resonator, the length of the resonator is selected relative to the wavelength of the microwave radiation used. n is preferably an integer from 1 to 200, more preferably from 2 to 100, particularly from 3 to 50, especially from 4 to 20, for example three, four, five, six, seven, eight, nine or ten.

The $E_{01n}$ mode of the cavity resonator is also referred to in English as the $TM_{01n}$ mode; see, for example, K. Lange, K. H. Löcherer, "Taschenbuch der Hochfrequenztechnik" [Handbook of High-Frequency Technology], volume 2, pages K21 ff.

The microwave energy can be injected into the hollow conductor which functions as the microwave applicator through holes or slots of suitable dimensions. In an embodiment particularly preferred in accordance with the invention, the reaction mixture is irradiated with microwaves in a reaction tube present in a hollow conductor with a coaxial transition of the microwaves. Microwave devices particularly preferred for this process are formed from a cavity resonator, a coupling device for injecting a microwave field into the cavity resonator and with one orifice each on two opposite end walls for passage of the reaction tube through the resonator. The microwaves are preferably injected into the cavity resonator by means of a coupling pin which projects into the cavity resonator. The coupling pin is preferably configured as a preferably metallic inner conductor tube which functions as a coupling antenna. In a particularly preferred embodiment, this coupling pin projects through one of the end orifices into the cavity resonator. The reaction tube more preferably adjoins the inner conductor tube of the coaxial transition, and is especially conducted through the cavity thereof into the cavity resonator. The reaction tube is preferably aligned axially with a central axis of symmetry of the cavity resonator. For this purpose, the cavity resonator preferably has one central orifice each on two opposite end walls for passage of the reaction tube.

The microwaves can be fed into the coupling pin or into the inner conductor tube which functions as a coupling antenna, for example, by means of a coaxial connecting line. In a preferred embodiment, the microwave field is supplied to the resonator via a hollow conductor, in which case the end of the coupling pin projecting out of the cavity resonator is conducted into the hollow conductor through an orifice in the wall of the hollow conductor, and takes microwave energy from the hollow conductor and injects it into the resonator.

In a specific embodiment, the reaction mixture is irradiated with microwaves in a microwave-transparent reaction tube which is axially symmetric within an $E_{01n}$ round hollow conductor with a coaxial transition of the microwaves. The reaction tube is conducted through the cavity of an inner conductor tube which functions as a coupling antenna into the cavity resonator. In a further preferred embodiment, the reaction mixture is irradiated with microwaves in a microwave-transparent reaction tube which is conducted through an $E_{01n}$ cavity resonator with axial introduction of the microwaves, the length of the cavity resonator being such as to form n=2 or more field maxima of the microwave. In a further preferred embodiment, the reaction mixture is irradiated with microwaves in a microwave-transparent reaction tube which is conducted through an $E_{01n}$ cavity resonator with axial introduction of the microwaves, the length of the cavity resonator being such as to form a standing wave where n=2 or more field maxima of the microwave. In a further preferred embodiment, the reaction mixture is irradiated with microwaves in a microwave-transparent reaction tube which is axially symmetric within a circular cylindrical $E_{01n}$ cavity resonator with a coaxial transition of the microwaves, the length of the cavity resonator being such as to form n=2 or more field maxima of the microwave. In a further preferred embodiment, the reaction mixture is irradiated with microwaves in a microwave-transparent reaction tube which is axially symmetric within a circular cylindrical $E_{01n}$ cavity resonator with a coaxial transition of the microwaves, the length of the cavity resonator being such as to form a standing wave where n=2 or more field maxima of the microwave.

Microwave generators, for example the magnetron, the klystron and the gyrotron, are known to those skilled in the art.

The reaction tubes used for microwave irradiation are preferably manufactured from microwave-transparent, high-melting material. Particular preference is given to using non-metallic reaction tubes. "Microwave-transparent" is understood here to mean materials which themselves absorb a minimum amount of microwave energy and convert it to heat. A measure employed for the ability of a substance to absorb microwave energy and convert it to heat is often the dielectric loss factor tan $\delta = \epsilon''/\epsilon'$. The dielectric loss factor tan $\delta$ is defined as the ratio of dielectric loss $\epsilon''$ to dielectric constant $\epsilon'$. Examples of tan $\delta$ values of different materials are reproduced, for example, in D. Bogdal, Microwave-assisted Organic Synthesis, Elsevier 2005. For reaction tubes suitable in accordance with the invention, materials with tan $\delta$ values measured at 2.45 GHz and 25° C. of less than 0.01, particularly less than 0.005 and especially less than 0.001 are preferred. Preferred microwave-transparent and thermally stable materials include primarily mineral-based materials, for example quartz, aluminum oxide, sapphire, zirconium oxide, silicon nitride and the like. Other suitable tube materials are thermally stable plastics, such as especially fluoropolymers, for example Teflon, and industrial plastics such as polypropylene, or polyaryl ether ketones, for example glass fiber-reinforced polyetheretherketone (PEEK). In order to withstand the temperature conditions during the reaction, minerals, such as quartz or aluminum oxide, coated with these plastics have been found to be especially suitable as reactor materials.

Inventive reaction tubes particularly suitable for the microwave irradiation have an internal diameter of one millimeter to approx. 50 cm, particularly between 2 mm and 35 cm, especially between 5 mm and 15 cm, for example between 10 mm and 7 cm. Reaction tubes are understood here to mean vessels whose ratio of length to diameter is greater than 5, preferably between 10 and 100 000, more preferably between 20 and 10 000, for example between 30 and 1000. The length of the reaction tube is understood here to mean the length of the tube over which the microwave irradiation proceeds.

$E_{01}$ cavity resonators particularly suitable in accordance with the invention preferably have a diameter which corresponds to at least half the wavelength of the microwave radiation used. The diameter of the cavity resonator is preferably 1.0 to 10 times, more preferably 1.1 to 5 times and especially 2.1 to 2.6 times half the wavelength of the microwave radiation used. The $E_{01}$ cavity resonator preferably has a round cross section, which is also referred to as an $E_{01}$ round hollow conductor. It more preferably has a cylindrical shape and especially a circular cylindrical shape.

The residence time of the reaction mixture in the region of the reaction tube exposed to the microwave irradiation (heating zone) depends on various factors, for example the geometry of the reaction tube, the incident microwave energy, the specific microwave absorption of the reaction mixture and the desired reaction temperature. The residence time of the reaction mixture in the reaction tube and especially in the heating zone is typically less than 30 minutes, preferably between 0.01 second and 15 minutes, more preferably between 0.1 second and 10 minutes and especially between 1 second and 5 minutes, for example between 5 seconds and 2 minutes. The intensity (power) of the microwave radiation is adjusted such that the reaction mixture when leaving the reaction tube has the desired reaction temperature.

The microwave power to be injected into the cavity resonator for the performance of the process according to the invention depends especially on the target reaction temperature, but also on the geometry of the reaction tube and hence the reaction volume and the flow rate of the reaction mixture through the reaction tube and the duration of the irradiation required for performance of the chemical reaction. The microwave power to be injected is typically between 200 W and several hundreds of kW and especially between 500 W and 100 kW, for example between 1 kW and 70 kW. It can be generated by means of one or more microwave generators. To optimize the space-time yield, the microwave power is preferably adjusted such that the reaction mixture attains the desired reaction temperature within a very short time, but without resulting in electrical discharges in the microwave applicator.

Preferably, the temperature rise caused by the microwave irradiation is limited to a maximum of 500° C., for example by regulating the microwave intensity and/or the flow rate. The temperature can be measured, for example, at the surface of the reaction tube; it is preferably determined in the reaction mixture directly after it leaves the heating zone. It has been found to be particularly useful to perform the process according to the invention at temperatures between 100 and 400° C., particularly between 120 and 350° C. and especially between 150 and 300° C., for example at temperatures between 180 and 270° C. In a preferred embodiment, the reaction product, directly after the microwave irradiation has ended, is cooled very rapidly to temperatures below 120° C., preferably below 100° C. and especially below 60° C.

In the reaction zone, reactant, product, any by-product and, if present, solvent can lead to a pressure buildup as a result of the temperature increase. This elevated pressure can be utilized in the course of decompression for volatilization and removal of excess reactant(s), product, by-product and optionally solvent, and/or for cooling of the reaction product.

The conversion of the reaction mixture is often not yet at chemical equilibrium when it leaves the reaction tube. In a preferred embodiment, the reaction mixture is therefore, after passing through the reaction tube, transferred directly, i.e. without intermediate cooling, into an isothermal reaction zone in which it is kept at reaction temperature for a certain time. Preferably, the isothermal reaction zone is also filled with open-pore foam which is catalytically active or comprises catalytically active species. Only after leaving the reaction zone is the reaction mixture optionally decompressed and cooled. Direct transfer from the reaction tube to the isothermal reaction zone is understood to mean that no active measures are taken for supply and more particularly for removal of heat between reaction tube and reaction zone. Preferably, the temperature difference between departure from the reaction tube and entry into the reaction zone is less than ±30° C., preferably less than ±20° C., more preferably less than ±10° C. and especially less than ±5° C. In a specific embodiment, the temperature of the reaction mixture on entry into the reaction zone corresponds to the temperature on departure from the reaction tube. This embodiment enables rapid and controlled heating of the reaction mixture to the desired reaction temperature without partial overheating, and then residence at this reaction temperature for a defined period before it is cooled. For instance, it is possible to achieve an elevated space-time yield, an elevated energy efficiency and additionally safe and reproducible operation. In this embodiment, the reaction mixture is preferably, directly after leaving the reaction zone, cooled very rapidly to temperatures below 120° C., preferably below 100° C. and especially below 60° C.

Useful isothermal reaction zones include all chemically inert vessels which enable residence of the reaction mixtures at the temperature established in the reaction tube. An isothermal reaction zone is understood to mean that the temperature of the reaction mixture in the reaction zone relative to the entrance temperature is kept constant within ±30° C., preferably within ±20° C., more preferably within ±10° C. and especially within ±5° C. Thus, the reaction mixture when leaving the reaction zone has a temperature which deviates from the temperature on entry into the reaction zone by not more than ±30° C., preferably ±20° C., more preferably ±10° C. and especially ±5° C.

In addition to continuous stirred tanks and tank cascades, especially tubes are suitable as the isothermal reaction zone. These reaction zones may consist of different materials, for example metals, ceramic, glass, quartz or plastics, with the proviso that they are mechanically stable and chemically inert under the selected temperature and pressure conditions. It has been found that thermally insulated vessels are particularly useful. The residence time of the reaction mixture in the reaction zone can be adjusted, for example, via the volume of the reaction zone. In the case of use of stirred tanks and tank cascades, it has been found to be equally useful to establish the residence time via the fill level of the tanks. In a preferred embodiment, the isothermal reaction zone is also laden with open-pore foam which is catalytically active or comprises catalytically active species. This may be the same foam as in the reaction tube or a different foam.

In a preferred embodiment, the reaction zone used is a tube. This may be an extension of the microwave-transparent reaction tube downstream of the heating zone, or else a separate tube of the same or different material connected to the reaction tube. For a given flow rate, the residence time of the reaction mixture can be determined over the length of the tube and/or cross section thereof. The tube which functions as the reaction zone is thermally insulated in the simplest case, such that the temperature which exists on entry of the reaction mixture into the reaction zone is held within the limits given above. However, it is also possible, for example by means of a heat carrier or cooling medium, to supply energy in a controlled manner to the reaction mixture in the reaction zone, or remove it therefrom. This embodiment has been found to be useful especially for startup of the apparatus or of the process. For example, the reaction zone may be configured as a tube coil or as a tube bundle which is within a heating or cooling bath or is charged with a heating or cooling medium in the form of a jacketed tube. The reaction zone may also be within a further microwave applicator in which the reaction mixture is treated once again with microwaves. In this case, it is possible to use either monomode or multimode applicators.

The residence time of the reaction mixture in the isothermal reaction zone depends on the reaction rate of the reaction conducted and the rate of any unwanted side reactions. In the ideal case, the residence time in the reaction zone is such that the thermal equilibrium state defined by the prevailing conditions is attained. Typically, the residence time is between 1 second and 10 hours, preferably between 10 seconds and 2 hours, more preferably between 20 seconds and 60 minutes, for example between 30 seconds and 30 minutes. Additionally preferably, the ratio between residence time of the reaction mixture in the reaction zone and residence time in the heating zone is between 1:2 and 100:1, more preferably 1:1 to 50:1 and especially between 1:1.5 and 10:1.

The inventive apparatus is typically provided at the inlet with a metering pump and a manometer, and, at the outlet, with a pressure-retaining device and a cooling device, for example a heat exchanger. This enables reactions within a very wide pressure and temperature range.

The cooling of the reaction mixture after departure from the reaction tube or the isothermal reaction zone can be effected, for example, by means of heat exchangers or adiabatic expansion or dilution with cold solvent. Typically, the reaction mixture is decompressed to atmospheric pressure, but it can also be decompressed to higher or lower pressures for subsequent process steps or in the case of use of specific apparatuses. For example, it has been found to be useful to decompress the reaction mixture to pressures well below atmospheric pressure for removal of solvent and/or unconverted reactants. Depending on the properties of the converted products and the further process steps provided, the cooling can be effected before or else after lowering the pressure, or at an intermediate pressure.

The preparation of the reaction mixtures can be performed continuously, batchwise, or else in semi-batchwise processes. For instance, the preparation of the reaction mixture can be performed in an upstream (semi)batchwise process, for example in a stirred tank. The reaction mixture may comprise one or more reactants, preferably two to ten, for example two, three, four, five, six or more reactants, and optionally assistants such as solvents and further, preferably homogeneous, catalysts and/or cocatalysts. The reaction mixture is preferably produced in situ and not isolated. In a preferred embodiment, the reactants, independently optionally diluted with solvent, are not mixed until shortly before entry into the reaction tube. For instance, it has been found to be particularly useful to combine the components of the reaction mixture in a mixing zone, from which they are conveyed into the heating zone, optionally after intermediate cooling. Additionally preferably, the reactants are supplied to the process according to the invention in liquid form. For this purpose, it is possible to use relatively high-melting and/or relatively high-viscosity reactants, for example in the molten state and/or admixed with solvent, for example as a solution, dispersion or emulsion. A further catalyst, if used, can be added to one of the reactants or else to the reactant mixture before entry into the reaction tube. It is also possible to convert gaseous and heterogeneous systems by the process according to the invention, in which case appropriate technical devices are required to convey the reaction mixture. The particle size of solid constituents of the reaction mixture must be well below the pore size of the foam. Preferably, the particle size of solid constituents, if present, is at most 50%, especially at most 10%, for example at most 2%, of the pore size of the foam.

In a specific embodiment, one or more gaseous reactants are used. Examples of suitable gaseous reactants are hydrogen, oxygen, chlorine, fluorine, ethylene oxide, propylene oxide, carbon monoxide, carbon dioxide, sulfur dioxide, hydrogen sulfide, ammonia, methylamine, dimethylamine, hydrazine and hydrogen chloride. These are preferably conveyed to the other reactants with an appropriate pump before the reaction mixture enters the reaction tube. Preferably, in the case of use of gaseous reactants, the reaction conditions are selected such that the gases are in the liquid state or dissolved in the reaction mixture. Alternatively, the gases can also be prepared in the heating zone by reaction of appropriate compounds and intervene in the actual reaction in situ. For example, hydrogenations can be performed either with molecular hydrogen or by transfer hydrogenations, for example with formates as the hydrogen donor. In the course of passage of the foam which is catalytically active and/or bears catalytically active species, excellent mixing of the reactants and intensive contact of the reaction mixture with the foam which is catalytically active and/or bears catalytically active species take place. Due to the compressive strength of the system, it is also possible to work under high pressures without any escape, more particularly, of the gaseous components or other low-boiling components.

To avoid side reactions and to prepare products of maximum purity, it has been found to be useful to handle reactants and products in the presence of an inert protective gas, for example nitrogen, argon or helium.

The reaction mixture can be fed into the reaction tube either at the end conducted through the inner conductor tube or at the opposite end.

By varying tube cross section, length of the irradiation zone (this is understood to mean the zone of the reaction tube in which the reaction mixture is exposed to microwave radiation), flow rate, geometry of the cavity resonator, of the incident microwave power and of the temperature attained, the reaction conditions are adjusted such that the desired reaction temperature is attained as rapidly as possible and the residence time at maximum temperature remains sufficiently short that as low as possible a level of side reactions or further reactions occurs. The reaction conditions desired for the individual chemical reaction are preferably regulated by control of the temperature of the reaction mixture attained at the end of the heating zone via the incident microwave power. The pressure is set by means of the decompression valve (pressure-retaining device) at the end of the reaction zone to a sufficiently high level that the reaction mixture including products and by-products obtained does not boil. In the presence of gaseous reactants, the concentration thereof and the pressure in the reaction tube are preferably adjusted such that the gaseous reactants are present dissolved in the reaction mixture or in liquefied form.

The process is performed preferably at pressures between 1 bar (atmospheric pressure) and 500 bar and more preferably between 1.5 and 200 bar, particularly between 3 bar and 150 bar and especially between 10 bar and 100 bar, for example between 15 bar and 50 bar. It has been found to be particularly useful to work under elevated pressure, in which case the temperature employed is above the boiling temperature (at standard pressure) of the reactants, products, of any solvent present and/or of the products formed during the reaction. The pressure is more preferably set to a sufficiently high level that the reaction mixture remains in the liquid state and does not boil during the microwave irradiation.

The inventive apparatus and the inventive process allow a very rapid, energy-saving and inexpensive performance of heterogeneously catalyzed chemical reactions in high yields in industrial scale amounts. The advantages of the inventive process lie especially in very rapid and nevertheless controlled heating of the reaction mixture by means of microwaves to the target reaction temperature without significant exceedance of the average temperature of the reaction mixture, for example at the vessel wall. This is particularly pronounced in the case of irradiation of the reaction mixture in the center of a symmetric microwave field within a reaction tube, the longitudinal axis of which is in the direction of propagation of the microwaves of a monomode microwave applicator, and especially within an $E_{01}$ cavity resonator, for example with a coaxial transition of the microwaves. With the inventive apparatus, in contrast to conventional heating techniques with heat transfer by means of a temperature gradient, it is possible to heat the reaction mixture virtually up to the decomposition temperature of the most thermally sensitive component and to maintain this temperature until the equilibrium state which exists for these conditions is established.

In the inventive apparatus and in the process which uses it, a very high efficiency is achieved in the exploitation of the microwave energy injected into the cavity resonator, and is typically above 50%, often above 80%, in some cases above 90% and in special cases above 95%, for example above 98%, of the incident microwave power, and thus offers economic and environmental advantages over conventional preparation processes, and also over prior art microwave processes.

Inventive apparatus and process additionally allow, through the continuous microwave irradiation of only small amounts, controlled by the volume of the apparatus, of reaction mixture, a controlled, safe and reproducible reaction regime. Especially in the case of irradiation of the reaction mixture in the center of a symmetric microwave field within a reaction tube whose longitudinal axis is in the direction of propagation of the microwaves of a monomode microwave applicator, the reaction mixture during the microwave irradiation is moved parallel to the direction of propagation of the microwaves. Thus, known overheating phenomena resulting from uncontrollable field distributions which can lead to local overheating as a result of varying intensities of the microwave field, for example at wave crests and node points, are balanced out by the flowing motion of the reaction mixture. The advantages mentioned also allow working with high microwave powers of, for example, more than 10 kW or more than 100 kW, and thus, in combination with only a short residence time in the cavity resonator, the accomplishment of large production volumes of 100 or more tonnes per year in one plant.

Compared to uncatalyzed microwave-supported reactions, and also compared to catalyzed, thermally heated reactions, shorter residence times of the reaction mixture in the reaction tube are required, as a result of which shorter and/or thinner microwave-transparent tubes are required to achieve a defined conversion. Virtually no formation of thermal decomposition products was observed, as arise in corresponding conversions in a flow tube of the same dimensions filled with open-pore foam which is catalytically active or comprises catalytically active species, with thermal jacket heating. In addition, in the products prepared by the process according to the invention, there are surprisingly very low contents of washed-out catalyst, and so there is typically no need for any further workup of the crude products. The use of open-pore foams as support material results in very good mixing of the reaction mixture by the cross-mixing caused by the open-cell foam, and turbulent flow is imparted in many cases. Thus, it is possible more particularly also to meter reactants which are immiscible or are only of limited mutual miscibility separately into the reaction tube directly before entry. This avoids the flow of the reactants past one another, which is often observed in the case of laminar flow, without any possibility of a reaction. Equally, the mixing even of reactants of incomplete mutual miscibility is also improved and a reaction is facilitated. In addition, foam-like structures possess a very large catalytically active surface area without offering any great flow resistance to the flowing reaction mixture, as exhibited by customary fixed bed catalysts in granular or other solid form. Thus, the use of the inventive apparatus and of the process which uses it lead to increased yields of target product and higher purity of the target product.

EXAMPLES

The irradiations of the reaction mixtures with microwaves were effected in an aluminum oxide reaction tube (60×1 cm) which was present in axial symmetry in a cylindrical cavity resonator (60×10 cm). The reaction tube was filled over the entire length with an open-cell foam specified in the respective examples. At one of the ends of the cavity resonator, the reaction tube ran through the cavity of an inner conductor tube which functions as a coupling antenna. The microwave field with a frequency of 2.45 GHz, generated by a magnetron, was injected into the cavity resonator by means of the coupling antenna ($E_{01}$ cavity applicator; monomode), in which a standing wave formed. After leaving this reaction tube, the reaction mixtures, unless stated otherwise, were decompressed to atmospheric pressure and cooled immediately to approx. 40° C. by means of an intensive heat exchanger.

The microwave power was adjusted over the experimental duration in each case in such a way that the desired temperature of the reaction mixture at the end of the reaction tube was kept constant. The microwave powers specified in the experimental descriptions therefore represent the mean value of the incident microwave power over time. The measurement of the temperature of the reaction mixture was undertaken by means of a Pt100 temperature sensor immediately after departure from the reaction tube (distance about 15 cm in an insulated stainless steel capillary, Ø 1 cm). Microwave energy not absorbed directly by the reaction mixture was reflected at the opposite end of the cavity resonator from the coupling antenna; the microwave energy which was also not absorbed by the reaction mixture on the return path and reflected back in the direction of the magnetron was passed with the aid of a prism system (circulator) into a water-containing vessel. The difference between energy injected and heating of this water load was used to calculate the microwave energy introduced into the reaction mixture.

By means of a high-pressure pump and of a pressure-release valve, the reaction mixture in the reaction tube was placed under such a working pressure that was sufficient always to keep all reactants and products or condensation products in the liquid state. The reaction mixtures were pumped through the apparatus at a constant flow rate and the residence time in the reaction tube was adjusted by modifying the flow rate.

The products were analyzed by means of $^1$H NMR spectroscopy at 500 MHz in $CDCl_3$.

Example 1

Preparation of Rapeseed Oil Fatty Acid Methyl Ester

A 10 l Büchi stirred autoclave with stirrer, internal thermometer and pressure equalizer was initially charged with 4.4 kg of rapeseed oil (5 mol, MW 878 g/mol) and 1.12 kg of methanol (35 mol) were added. At a working pressure of 35 bar, the mixture thus obtained was pumped continuously at 5 l/h through a reaction tube which, for this experiment, was filled with an open-cell foam of cordierite with a pore count of 50 ppi and a porosity of 70%. It was exposed to a microwave power of 2.2 kW, 91% of which was absorbed by the reaction mixture. The residence time of the reaction mixture in the reaction tube was approx. 30 seconds. After leaving the reaction tube, the reaction mixture had a temperature of 211° C.

A conversion of the triglyceride of 97% of theory was attained. The reaction product was pale yellowish in color; the content of calcium ions thereof was below 5 ppm (<detection limit). After removal of the glycerol, which was of higher specific gravity, and distillative removal of the excess methanol, 4.2 kg of rapeseed oil fatty acid methyl ester were obtained, which contained 0.5% diglycerides and 1.3% monoglycerides as by-products.

Example 2

Suzuki Coupling

A nitrogen-inertized 10 l Büchi stirred autoclave with stirrer, internal thermometer and pressure equalizer was initially charged with 6 liters of a mixture of ethanol, water and dimethylformamide, and 1.13 kg of 4-bromotoluene (6.6 mol) and 732 g (6.0 mol) of phenylboric acid were dissolved therein. This was followed by inertization again with nitrogen. At a working pressure of 30 bar, the reactant solution thus obtained was pumped continuously at 3.8 l/h through the reaction tube filled with palladium-doped aluminum oxide foam. An aluminum oxide foam with a pore count of 40 ppi and a porosity of 60% had been impregnated with Pd for this experiment, based on the method of M. Organ (Angew. Chem. 2006, 118, 2827-2832). The reaction mixture was exposed to a microwave power of 1.8 kW, 95% of which was absorbed by the reaction mixture. The residence time of the reaction mixture in the reaction tube was approx. 39 seconds. After leaving the reaction tube, the reaction mixture had a temperature of 248° C.

A yield (based on the phenylboric acid used in deficiency) determined by means of $^1$H NMR of 75% of theory was attained; the palladium content of the product was <5 ppm (<detection limit). By means of a thin-film evaporator, the solvents used were removed and the product residue was transferred into a vacuum distillation apparatus. After distillative purification (134-136° C./12 mbar), 706 g of 4-methylbiphenyl were obtained with a purity of >99%.

Example 3

Catalytic Hydrogenation of Sunflower Oil

A nitrogen-inertized 10 l Büchi stirred autoclave with stirrer, internal thermometer and pressure equalizer was initially charged with 7 liters of sunflower oil with a proportion of unsaturated fatty acids of 90%, which were heated to 70° C. Subsequently, at a working pressure of 8 bar, the oil was pumped continuously at 4 liters per hour through the reaction tube which was filled with a Pd-doped aluminum oxide foam as described in example 2. Before the oil entered the reaction tube, hydrogen gas was injected into the reactant stream in such a way that the pressure of 8 bar which is established within the apparatus was not exceeded.

By means of a microwave power of 1.7 kW, a mean reaction temperature of 160° C. was established at the end of the reaction tube. The residence time of the oil/$H_2$ mixture in the reaction tube was 37 seconds on average. After leaving the reaction tube, the reaction product was cooled to 40° C. by means of a heat exchanger.

The resulting hydrogenated sunflower oil had, on completion of reaction, a content of unsaturated fatty acid of 7%. When left to stand, the product solidified after a short time to give a white, waxy mass.

Example 4

Catalytic Reduction of Cyclohexanone by Means of Transfer Hydrogenation to Cyclohexanol A nitrogen-inertized 10 l Büchi stirred autoclave with stirrer, internal thermometer and pressure equalizer was initially charged with 5 liters of isopropanol (anhydrous), 2.94 kg of cyclohexanone (30 mol) were added while stirring and the mixture was heated to 50° C. At a working pressure of 25 bar, the cyclohexanone solution thus prepared was then pumped at a flow rate of 3 liters per hour through the reaction tube filled with a ruthenium-impregnated cordierite foam with a pore count of 30 ppi and a porosity of 60%.

The incident microwave power of 1.5 kW heated the reaction mixture to 155° C. The residence time of the isopropanol/cyclohexanone solution in the reaction tube was approximately one minute. After leaving the reaction tube, the reaction product was cooled to 40° C. by means of a heat exchanger. The yield determined by $^1$H NMR was 93% based on the cyclohexanone used. The ruthenium content of the reaction product was <5 ppm (<detection limit).

Example 5

Desulfurization of Diesel

A 10 l Büchi stirred autoclave with stirrer, internal thermometer and pressure equalizer was initially charged with 8 liters of a middle distillate fraction ("diesel") with a boiling range from 160 to 365° C. and a sulfur content of 1000 ppm, and inertized with nitrogen. At a working pressure of 20 bar, the sulfur-containing diesel was pumped continuously at a flow rate of 5 l/h through the reaction tube which, for this experiment, was filled with an open-cell foam composed of an aluminum oxide permeated by silicon carbide and having a pore count of 75 ppi with a porosity of 60%, to which a mixture of cobalt oxide and molybdenum oxide had been applied and converted to a sulfide form. Prior to entry of the diesel into the reaction tube, $H_2$ was injected into the diesel stream by means of a suitable metering device (1.5 liters/h based on standard pressure). A microwave power of 3 kW was applied, 85% of which was absorbed by the reaction mixture. The residence time of the reaction mixture in the reaction tube was approx. 30 seconds. After leaving the reaction tube, the reaction mixture had a temperature of 275° C. By means of a heat exchanger, before the decompression of the system, the product was cooled to 60° C. and then decompressed into a degassing vessel in which the hydrogen sulfide formed and residues of unreacted hydrogen were stripped out by passing nitrogen through. The diesel thus obtained had a residual sulfur content of 35 ppm.

The invention claimed is:

1. An apparatus for continuous performance of heterogeneously catalyzed chemical reactions, wherein the apparatus comprises
a monomode microwave applicator configured to propagate microwave radiation in a direction of propagation;
a substantially microwave-transparent reaction tube having a longitudinal axis in the direction of propagation of the monomode microwave applicator, and having an irradiation zone operatively coupled to the monomode microwave applicator; and
an open-cell solid foam essentially filling the reaction tube in the irradiation zone, wherein the open-cell solid foam comprises a plurality of cells and a plurality of cell walls, the cells and the cell walls forming two continuous networks that penetrate one another, and has a porosity of at least 20%.

2. The apparatus as claimed in claim 1, wherein the monomode microwave applicator comprises a hollow conductor in which the microwave-transparent reaction tube is disposed, the hollow conductor being operatively connected to a microwave generator.

3. The apparatus as claimed in claim 1, in which the monomode microwave applicator is configured as a cavity resonator.

4. The apparatus as claimed in claim 1, in which the monomode microwave applicator is configured as a cavity resonator of the reflection type.

5. The apparatus as claimed in claim 2, in which the hollow conductor has a central axis of symmetry, and wherein the reaction tube is aligned axially with the central axis of symmetry of the hollow conductor.

6. The apparatus as claimed in claim 3, wherein the cavity resonator comprises a coaxial transition of the microwaves.

7. The apparatus as claimed in claim 3, in which the cavity resonator is configured such that it can be operated in $E_{01n}$ mode with respect to the microwave radiation where n is an integer from 1 to 200.

8. The apparatus as claimed in claim 3, in which the cavity resonator is configured such that a standing wave with respect to the microwave radiation can form therein.

9. The apparatus as claimed in claim 1, in which the open-cell solid foam consists of a ceramic material which is itself catalytically active.

10. The apparatus as claimed in claim 1, in which the open-cell solid foam is a ceramic material which bears a different catalytically active species.

11. The apparatus as claimed in claim 1, in which the open-cell solid foam consists of a catalytically active metal.

12. The apparatus as claimed in claim 1, in which the pore count of the open-cell solid foam, determined on the basis of ASTM D3576, is between 1 and 150 ppi.

13. The apparatus as claimed in claim 1, in which the porosity of the open-cell solid foam is 50% to 90%.

14. The apparatus as claimed in claim 1, in which the pore size of the open-cell solid foam is between 0.01 mm and 1 cm.

15. The apparatus as claimed in claim 1, in which the average strength of the open-cell solid foam, determinable by means of die indentation, is between 100 and 15 000 N.

16. The apparatus as claimed in claim 1, in which the open-cell solid foam bears or consists of catalytically active species, and is configured such that a reaction mixture to be converted can flow through it.

17. The apparatus as claimed in claim 1, wherein the open-cell solid foam is formed from a catalytically active material.

18. The apparatus as claimed in claim 1, wherein the open-cell solid foam is formed from a material into which catalytically active species have been intercalated and/or which has been coated or impregnated with catalytically active species.

19. The apparatus as claimed in claim 1, wherein the open-cell solid foam is formed from a ceramic material into which catalytically active species have been intercalated and/or which has been coated or impregnated with catalytically active species.

20. The apparatus as claimed in claim 1, wherein the open-core solid foam is fixed in the reaction tube as a core.

* * * * *